(12) United States Patent
Kowalik et al.

(10) Patent No.: US 12,268,901 B2
(45) Date of Patent: Apr. 8, 2025

(54) TARGETING CELL TROPISM RECEPTORS TO INHIBIT CYTOMEGALOVIRUS INFECTION

(71) Applicant: UNIVERSITY OF MASSACHUSETTS, Boston, MA (US)

(72) Inventors: Timothy F. Kowalik, Princeton, MA (US); Xiaofei E, Westborough, MA (US); Abraham L Brass, Newton, MA (US)

(73) Assignee: University of Massachusetts, Westborough, MA (US)

( * ) Notice: Subject to any disclaimer, the term of this patent is extended or adjusted under 35 U.S.C. 154(b) by 291 days.

(21) Appl. No.: 17/933,709

(22) Filed: Sep. 20, 2022

(65) Prior Publication Data

US 2023/0034732 A1    Feb. 2, 2023

Related U.S. Application Data

(62) Division of application No. 16/604,735, filed as application No. PCT/US2018/027469 on Apr. 13, 2018, now Pat. No. 11,484,570.

(60) Provisional application No. 62/485,742, filed on Apr. 14, 2017.

(51) Int. Cl.
| | | |
|---|---|---|
| *A61K 31/52* | (2006.01) | |
| *A61K 38/17* | (2006.01) | |
| *A61P 31/12* | (2006.01) | |
| *C07K 16/08* | (2006.01) | |
| *C07K 16/28* | (2006.01) | |
| *C12N 15/113* | (2010.01) | |

(52) U.S. Cl.
CPC ............ *A61K 31/52* (2013.01); *A61K 38/177* (2013.01); *A61P 31/12* (2018.01); *C07K 16/089* (2023.08); *C07K 16/28* (2013.01); *C12N 15/1138* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| | | |
|---|---|---|
| 11,484,570 B2 | 11/2022 | Kowalik et al. |
| 2004/0248839 A1 | 12/2004 | Kowalik |
| 2007/0009916 A1 | 1/2007 | Suwa et al. |
| 2013/0108649 A1 | 5/2013 | Robinson et al. |
| 2013/0323835 A1 | 12/2013 | McDonald et al. |
| 2015/0313878 A1 | 11/2015 | Robinson et al. |
| 2020/0376077 A1 | 12/2020 | Kowalik et al. |

FOREIGN PATENT DOCUMENTS

| | | |
|---|---|---|
| WO | WO 1996/01107 | 1/1996 |
| WO | WO 2004/071430 | 8/2004 |
| WO | WO 2010/007533 | 1/2010 |
| WO | WO 2014/071430 | 5/2014 |
| WO | WO 2016/030378 | 3/2016 |

OTHER PUBLICATIONS

Adler et al., "Role of human cytomegalovirus UL131A in cell type-specific virus entry and release," Journal of General Virology, Sep. 1, 2006, 87(9):2451-60.
Chiuppesi et al., "Vaccine-derived neutralizing antibodies to the human cytomegalovirus gH/gL pentamer potently block primary cytotrophoblast infection," Journal of Virology, Dec. 1, 2015, 89(23):11884-98.
Demmler, "Infectious Diseases Society of America and Centers for Disease Control: summary of a workshop on surveillance for congenital cytomegalovirus disease," Reviews of Infectious Diseases, Mar. 1, 1991, 13(2):315-29.
E et al., "A novel DDB2-ATM feedback loop regulates human cytomegalovirus replication," Journal of virology, Feb. 15, 2014, 88(4):2279-90.
E et al., "An E2F1-mediated DNA damage response contributes to the replication of human cytomegalovirus," PLoS Pathogens, May 12, 2011, 7(5):e1001342, 11 pages.
EP Extended Search Report in European Appln. No. 18784005.3, dated May 14, 2021, 7 pages.
EP Supplementary European Search Report in European Appln. No. 18784005.3, dated Feb. 11, 2021, 14 pages.
Gault et al., "Quantification of human cytomegalovirus DNA by real-time PCR," Journal of Clinical Microbiology, Feb. 1, 2001, 39(2):772-5.
Hanfler et al., "Quantitation of cytomegalovirus (hCMV) DNA and beta-actin DNA by duplex real-time fluorescence PCR in solid organ (liver) transplant recipients," Medical Microbiology and Immunology, Nov. 2003, 192:197-204.
International Search Report and Written Opinion in International Appln. No. PCT/US2018/027469, dated Jul. 24, 2018, 14 pages.
Istas et al., "Surveillance for congenital cytomegalovirus disease: a report from the National Congenital Cytomegalovirus Disease Registry," Clinical Infectious Diseases, Mar. 1, 1995, 20(3):665-70.
Kim et al., "Viral binding-induced signaling drives a unique and extended intracellular trafficking pattern during infection of primary monocytes," Proceedings of the National Academy of Sciences, Aug. 2, 2016, 113(31):8819-24.
Lee et al. "US28, a Virally-Encoded GPCR as an Antiviral Target for Human Cytomegalovirus Infection," Biomol Ther, Jan. 1, 2017 {Jan. 1, 2017), vol. 25, No. 1. pp. 69-79.
Malinger et al., "Fetal cytomegalovirus infection of the brain: the spectrum of sonographic findings," American Journal of Neuroradiology, Jan. 1, 2003, 24(1):28-32.
Merigan, "Treatment of AIDS with combinations of antiretroviral agents," The American Journal of Medicine, Apr. 10, 1991, 90(4):S8-17.

(Continued)

*Primary Examiner* — Ruixiang Li
(74) *Attorney, Agent, or Firm* — Fish & Richardson P.C.

(57) ABSTRACT

Methods for treating or reducing the risk of a cytomegalovirus infection in a subject that include administering one or more of an inhibitor of Deleted in Malignant Brain Tumors 1 (DMBT1), an inhibitor of OR14I1, or an inhibitor of adenylyl cyclases.

5 Claims, 29 Drawing Sheets

Specification includes a Sequence Listing.

(56) References Cited

OTHER PUBLICATIONS

Miazzi et al., "Odor-induced cAMP production in *Drosophila melanogaster* olfactory sensory neurons," Journal of Experimental Biology, Jun. 15, 2016, 219.12 (2016):1798-1803.

Paredes et al., "Human cytomegalovirus: bacterial artificial chromosome (BAC) cloning and genetic manipulation," Current Protocols in Microbiology, Feb. 2012, 24(1):14E-4, 33 pages.

Perreira et al., "Functional genomic strategies for elucidating human-virus interactions: will CRISPR knockout RNAi and haploid cells?," Advances in Virus Research, Jan. 1, 2016, 1;94:1-51.

Pinto et al., "Activation and inhibition of adenylyl cyclase isoforms by forskolin analogs," Journal of Pharmacology and Experimental Therapeutics, Apr. 1, 2008, 325(1):27-36.

Ryckman et al., "HCMV gH/gL/UL128-131 interferes with virus entry into epithelial cells: evidence for cell type-specific receptors," Proceedings of the National Academy of Sciences, Sep. 16, 2008, 105(37):14118-23.

Ryckman et al., "Human cytomegalovirus entry into epithelial and endothelial cells depends on genes UL128 to UL150 and occurs by endocytosis and low-pH fusion," Journal of Virology, Jan. 15, 2006, 80(2):710-22.

Savidis et al. "Identification of Zika Virus and Dengue Virus Dependency Factors using Functional Genomics," Cell Reports, Jun. 28, 2016 (Jun. 28, 2016), vol. 16, pp. 232-246.

Shalem et al., "Genome-scale CRISPR-Cas9 knockout screening in human cells," Science, Jan. 3, 2014, 343(6166):84-7.

Shih et al., "Chimeric human immunodeficiency virus type 1/type 2 reverse transcriptases display reversed sensitivity to nonnucleoside analog inhibitors," Proceedings of the National Academy of Sciences, Nov. 1, 1991, 88(21):9878-82.

Tao et al., "Frizzled proteins are colonic epithelial receptors for C. difficile toxin B." Nature, Oct. 20, 2016, 538(7625):350-5.

Wang et al., "Delivery of Cas9 protein into mouse zygotes through a series of electroporation dramatically increases the efficiency of model creation," Journal of Genetics and Genomics. May 20, 2016, 43(5):319-27.

Wang et al., "Human cytomegalovirus UL131 open reading frame is required for epithelial cell tropism," Journal of Virology, Aug. 15, 2005, 79(16):10330-8.

Wang et al., "Human cytomegalovirus virion protein complex required for epithelial and endothelial cell tropism," Proceedings of the National Academy of Sciences, Dec. 13, 2005, 102(50):18153-8.

White et al., "A TIBO derivative, R82913, is a potent inhibitor of HIV-1 reverse transcriptase with heteropolymer templates," Antiviral Research, Oct. 1, 1991, 16(3):257-66.

Xiaofei E et al., OR14I1 is a receptor for the human cytomegalovirus pentanneric complex and defines viral epithelial cell tropism. Proc Natl Acad Sci USA 116(14):7043-7052, 2019.

Yu et al., "Construction of a self-excisable bacterial artificial chromosome containing the human cytomegalovirus genome and mutagenesis of the diploid TRL/IRL13 gene," Journal of Virology, Mar. 1, 2002, 76(5):2316-28.

EP Office Action in European Appln. No. 18784005.3, mailed on Aug. 29, 2023, 8 pages.

SEQUENCE LISTING

```
Sequence total quantity: 53
SEQ ID NO: 1          moltype = AA  length = 26
FEATURE               Location/Qualifiers
REGION                1..26
                      note = N-terminal fragment of OR14I1
source                1..26
                      mol_type = protein
                      organism = synthetic construct
SEQUENCE: 1
MDNLTKVTEF LLMEFSGIWE LQVLHA                                         26

SEQ ID NO: 2          moltype = AA  length = 311
FEATURE               Location/Qualifiers
source                1..311
                      mol_type = protein
                      organism = Homo sapiens
```

```
SEQUENCE: 2
MDNLTKVTEF LLMEFSGIWE LQVLHAGLFL LIYLAVLVGN LLIIAVITLD QHLHTPMYFF    60
LKNLSVLDLC YISVTVPKSI RNSLTRRSSI SYLGCVAQVY FFSAFASAEL AFLTVMSYDR   120
YVAICHPLQY RAVMTSGGCY QMAVTTWLSC FSYAAVHTGN MFREHVCRSS VIHQFFRDIP   180
HVLALVSCEV FFVEFLTLAL SSCLVLGCFI LMMISYFQIF STVLRIPSGQ SRAKAFSTCS   240
PQLIVIMLFL TTGLFAALGP IAKALSIQDL VIALTYTVLP PFLNPIIYSL RNKEIKTAMW   300
RLFVKIYFLQ K                                                       311

SEQ ID NO: 3              moltype = AA  length = 13
FEATURE                   Location/Qualifiers
REGION                    1..13
                          note = OR14I1 peptide
source                    1..13
                          mol_type = protein
                          organism = synthetic construct
SEQUENCE: 3
FLLMEFSGIW ELQ                                                      13

SEQ ID NO: 4              moltype = AA  length = 13
FEATURE                   Location/Qualifiers
REGION                    1..13
                          note = OR14I1 peptide
source                    1..13
                          mol_type = protein
                          organism = synthetic construct
SEQUENCE: 4
LLMEFSGIWE LQV                                                      13

SEQ ID NO: 5              moltype = AA  length = 13
FEATURE                   Location/Qualifiers
REGION                    1..13
                          note = OR14I1 peptide
source                    1..13
                          mol_type = protein
                          organism = synthetic construct
SEQUENCE: 5
LMEFSGIWEL QVL                                                      13

SEQ ID NO: 6              moltype = AA  length = 11
FEATURE                   Location/Qualifiers
REGION                    1..11
                          note = OR14I1 peptide
source                    1..11
                          mol_type = protein
                          organism = synthetic construct
SEQUENCE: 6
LMEFSGIWEL Q                                                        11

SEQ ID NO: 7              moltype = AA  length = 11
FEATURE                   Location/Qualifiers
REGION                    1..11
                          note = QLEWIGSFEML
source                    1..11
                          mol_type = protein
                          organism = synthetic construct
SEQUENCE: 7
QLEWIGSFEM L                                                        11

SEQ ID NO: 8              moltype = DNA  length = 21
FEATURE                   Location/Qualifiers
misc_feature              1..21
                          note = primer with original sequence
source                    1..21
                          mol_type = other DNA
                          organism = synthetic construct
SEQUENCE: 8
tcctacgcag ccgtccacac t                                             21

SEQ ID NO: 9              moltype = DNA  length = 21
FEATURE                   Location/Qualifiers
misc_feature              1..21
                          note = primer with silent mutation sequence
source                    1..21
                          mol_type = other DNA
                          organism = synthetic construct
SEQUENCE: 9
agctatgctg ctgtgcatac c                                             21

SEQ ID NO: 10             moltype = DNA  length = 41
```

```
FEATURE                 Location/Qualifiers
misc_feature            1..41
                        note = primer lentiGP-1_F
source                  1..41
                        mol_type = other DNA
                        organism = synthetic construct
SEQUENCE: 10
aatggactat catatgctta ccgtaacttg aaagtatttc g                       41

SEQ ID NO: 11           moltype = DNA  length = 36
FEATURE                 Location/Qualifiers
misc_feature            1..36
                        note = primer lentiGP-3_R
source                  1..36
                        mol_type = other DNA
                        organism = synthetic construct
SEQUENCE: 11
atgaatactg ccatttgtct caagatctag ttacgc                             36

SEQ ID NO: 12           moltype = DNA  length = 16
FEATURE                 Location/Qualifiers
misc_feature            1..16
                        note = flanking sequence at 5' end
source                  1..16
                        mol_type = other DNA
                        organism = synthetic construct
SEQUENCE: 12
gaaaggacga aacacc                                                   16

SEQ ID NO: 13           moltype = DNA  length = 16
FEATURE                 Location/Qualifiers
misc_feature            1..16
                        note = flanking sequence at 3' end
source                  1..16
                        mol_type = other DNA
                        organism = synthetic construct
SEQUENCE: 13
tttctagctc taaaac                                                   16

SEQ ID NO: 14           moltype = DNA  length = 20
FEATURE                 Location/Qualifiers
misc_feature            1..20
                        note = guideRNA PDGFRA_1
source                  1..20
                        mol_type = other DNA
                        organism = synthetic construct
SEQUENCE: 14
gaccttcaat ggacttaccc                                               20

SEQ ID NO: 15           moltype = DNA  length = 20
FEATURE                 Location/Qualifiers
misc_feature            1..20
                        note = guideRNA PDGFRA_2
source                  1..20
                        mol_type = other DNA
                        organism = synthetic construct
SEQUENCE: 15
agctatgggg acttcccatc                                               20

SEQ ID NO: 16           moltype = DNA  length = 20
FEATURE                 Location/Qualifiers
misc_feature            1..20
                        note = guideRNA OR14I1_1
source                  1..20
                        mol_type = other DNA
                        organism = synthetic construct
SEQUENCE: 16
tcctacgcag ccgtccacac                                               20

SEQ ID NO: 17           moltype = DNA  length = 20
FEATURE                 Location/Qualifiers
misc_feature            1..20
                        note = guideRNA OR14I1_2
source                  1..20
                        mol_type = other DNA
                        organism = synthetic construct
SEQUENCE: 17
tgagcaccgt tgagaagatt                                               20
```

```
SEQ ID NO: 18            moltype = DNA   length = 20
FEATURE                  Location/Qualifiers
misc_feature             1..20
                         note = guideRNA DMBT1_1
source                   1..20
                         mol_type = other DNA
                         organism = synthetic construct
SEQUENCE: 18
ttaccgtagt ctgtagtcct                                                    20

SEQ ID NO: 19            moltype = DNA   length = 20
FEATURE                  Location/Qualifiers
misc_feature             1..20
                         note = guideRNA DMBT1_2
source                   1..20
                         mol_type = other DNA
                         organism = synthetic construct
SEQUENCE: 19
cgcagcttca ctgattccct                                                    20

SEQ ID NO: 20            moltype = DNA   length = 20
FEATURE                  Location/Qualifiers
misc_feature             1..20
                         note = guideRNA CON_1
source                   1..20
                         mol_type = other DNA
                         organism = synthetic construct
SEQUENCE: 20
cgggatgcag ctggagagga                                                    20

SEQ ID NO: 21            moltype = DNA   length = 20
FEATURE                  Location/Qualifiers
misc_feature             1..20
                         note = guideRNA CON_2
source                   1..20
                         mol_type = other DNA
                         organism = synthetic construct
SEQUENCE: 21
ccagttgctc tgggggaaca                                                    20

SEQ ID NO: 22            moltype = DNA   length = 21
FEATURE                  Location/Qualifiers
misc_feature             1..21
                         note = shOR14I1
source                   1..21
                         mol_type = other DNA
                         organism = synthetic construct
SEQUENCE: 22
gcagaagctc catctcttat c                                                  21

SEQ ID NO: 23            moltype = DNA   length = 21
FEATURE                  Location/Qualifiers
misc_feature             1..21
                         note = shDMBT1
source                   1..21
                         mol_type = other DNA
                         organism = synthetic construct
SEQUENCE: 23
ggagtcaact gtagcagaag g                                                  21

SEQ ID NO: 24            moltype = DNA   length = 21
FEATURE                  Location/Qualifiers
misc_feature             1..21
                         note = shPDGFRA
source                   1..21
                         mol_type = other DNA
                         organism = synthetic construct
SEQUENCE: 24
gcctttgtac ctctaggaat g                                                  21

SEQ ID NO: 25            moltype = DNA   length = 21
FEATURE                  Location/Qualifiers
misc_feature             1..21
                         note = hCON
source                   1..21
                         mol_type = other DNA
                         organism = synthetic construct
SEQUENCE: 25
aattttttc cccaaagggg g                                                   21
```

```
SEQ ID NO: 26            moltype = AA   length = 16
FEATURE                  Location/Qualifiers
REGION                   1..16
                         note = OR14I1 Peptide 2
source                   1..16
                         mol_type = protein
                         organism = synthetic construct
SEQUENCE: 26
PKSIRNSLTR RSSISY                                                    16

SEQ ID NO: 27            moltype = AA   length = 27
FEATURE                  Location/Qualifiers
REGION                   1..27
                         note = OR14I1 Peptide 3
source                   1..27
                         mol_type = protein
                         organism = synthetic construct
SEQUENCE: 27
REHVCRSSVI HQFFRDIPHV LALVSCE                                        27

SEQ ID NO: 28            moltype = AA   length = 7
FEATURE                  Location/Qualifiers
REGION                   1..7
                         note = OR14I1 Peptide 4
source                   1..7
                         mol_type = protein
                         organism = synthetic construct
SEQUENCE: 28
KALSIQD                                                              7

SEQ ID NO: 29            moltype = AA   length = 13
FEATURE                  Location/Qualifiers
REGION                   1..13
                         note = OR14I1 peptide 1-13aa
source                   1..13
                         mol_type = protein
                         organism = synthetic construct
SEQUENCE: 29
MDNLTKVTEF LLM                                                       13

SEQ ID NO: 30            moltype = AA   length = 13
FEATURE                  Location/Qualifiers
REGION                   1..13
                         note = OR14I1 peptide 2-14aa
source                   1..13
                         mol_type = protein
                         organism = synthetic construct
SEQUENCE: 30
DNLTKVTEFL LME                                                       13

SEQ ID NO: 31            moltype = AA   length = 13
FEATURE                  Location/Qualifiers
REGION                   1..13
                         note = OR14I1 peptide 3-15aa
source                   1..13
                         mol_type = protein
                         organism = synthetic construct
SEQUENCE: 31
NLTKVTEFLL MEF                                                       13

SEQ ID NO: 32            moltype = AA   length = 13
FEATURE                  Location/Qualifiers
REGION                   1..13
                         note = OR14I1 peptide 4-16aa
source                   1..13
                         mol_type = protein
                         organism = synthetic construct
SEQUENCE: 32
LTKVTEFLLM EFS                                                       13

SEQ ID NO: 33            moltype = AA   length = 13
FEATURE                  Location/Qualifiers
REGION                   1..13
                         note = OR14I1 peptide 5-17aa
source                   1..13
                         mol_type = protein
                         organism = synthetic construct
SEQUENCE: 33
```

-continued

```
TKVTEFLLME FSG                                                          13

SEQ ID NO: 34           moltype = AA  length = 13
FEATURE                 Location/Qualifiers
REGION                  1..13
                        note = OR14I1 peptide 6-18aa
source                  1..13
                        mol_type = protein
                        organism = synthetic construct
SEQUENCE: 34
KVTEFLLMEF SGI                                                          13

SEQ ID NO: 35           moltype = AA  length = 13
FEATURE                 Location/Qualifiers
REGION                  1..13
                        note = OR14I1 peptide 7-19aa
source                  1..13
                        mol_type = protein
                        organism = synthetic construct
SEQUENCE: 35
VTEFLLMEFS GIW                                                          13

SEQ ID NO: 36           moltype = AA  length = 13
FEATURE                 Location/Qualifiers
REGION                  1..13
                        note = OR14I1 peptide
source                  1..13
                        mol_type = protein
                        organism = synthetic construct
SEQUENCE: 36
TEFLLMEFSG IWE                                                          13

SEQ ID NO: 37           moltype = AA  length = 13
FEATURE                 Location/Qualifiers
REGION                  1..13
                        note = OR14I1 peptide 9-21aa
source                  1..13
                        mol_type = protein
                        organism = synthetic construct
SEQUENCE: 37
EFLLMEFSGI WEL                                                          13

SEQ ID NO: 38           moltype = AA  length = 13
FEATURE                 Location/Qualifiers
REGION                  1..13
                        note = OR14I1 peptide 10-22aa
source                  1..13
                        mol_type = protein
                        organism = synthetic construct
SEQUENCE: 38
FLLMEFSGIW ELQ                                                          13

SEQ ID NO: 39           moltype = AA  length = 13
FEATURE                 Location/Qualifiers
REGION                  1..13
                        note = OR14I1 peptide 11-23aa
source                  1..13
                        mol_type = protein
                        organism = synthetic construct
SEQUENCE: 39
LLMEFSGIWE LQV                                                          13

SEQ ID NO: 40           moltype = AA  length = 13
FEATURE                 Location/Qualifiers
REGION                  1..13
                        note = OR14I1 peptide
source                  1..13
                        mol_type = protein
                        organism = synthetic construct
SEQUENCE: 40
LMEFSGIWEL QVL                                                          13

SEQ ID NO: 41           moltype = AA  length = 13
FEATURE                 Location/Qualifiers
REGION                  1..13
                        note = OR14I1 peptide 13-25aa
source                  1..13
                        mol_type = protein
                        organism = synthetic construct
```

```
SEQUENCE: 41
MEFSGIWELQ VLH                                                           13

SEQ ID NO: 42           moltype = AA  length = 13
FEATURE                 Location/Qualifiers
REGION                  1..13
                        note = OR14I1 peptide 14-26aa
source                  1..13
                        mol_type = protein
                        organism = synthetic construct
SEQUENCE: 42
EFSGIWELQV LHA                                                           13

SEQ ID NO: 43           moltype = DNA  length = 936
FEATURE                 Location/Qualifiers
source                  1..936
                        mol_type = other DNA
                        organism = Homo sapiens
SEQUENCE: 43
atggacaatc tcacaaaagt gacagaattc ctgctgatgg agtttctgg tatctgggag         60
ctgcaggtgc tgcacgccgg gctgtttctg ctgatttatc tggcagtgct ggtggggaac       120
ctgctcatca ttgcagtcat cactctcgat cagcatcctt acacacccat gtacttcttc      180
ctgaagaacc tctccgtttt ggatctgtgc tacatctcag tcactgtgcc taaatccatc      240
cgtaactccc tgactcgcag aagctccatc tcttatcttg ctgtgtggc tcaagtctat        300
tttttctctg cctttgcatc tgctgagctg gccttcctta ctgtcatgtc ttatgaccgc       360
tatgttgcca tttgccaccc cctccaatac agagccgtga tgcatcagg agggtgctat        420
cagatggcag tcaccacctg gctaagctgc ttttcctacg cagccgtcca cactggcaac       480
atgtttcggg agcacgtttg cagatccagt gtgatccacc agtcttccg tgacatccct        540
catgtgttgg ccctggtttc ctgtgaggtt tctttgtag agttttgac cctggccctg         600
agctcatgct tggttctggg atgctttatt ctcatgatga tctcctattt ccaaatcttc       660
tcaacggtgc tcagaatccc ttcaggacag agtcgagcaa aagccttctc cacctgctcc       720
ccccagctca ttgtcatcat gctctttctt accacagggc tctttgctgc cttaggacca       780
attgcaaaag ctctgtccat tcaggattta gtgattgctc tgacatacac agttttgcct       840
cccttcctca atcccatcat atatagtctt aggaataagg agattaaaac agccatgtgg       900
agactctttg tgaagatata ttttctgcaa aagtag                                 936

SEQ ID NO: 44           moltype = DNA  length = 12
FEATURE                 Location/Qualifiers
misc_feature            1..12
                        note = exemplary sequence
source                  1..12
                        mol_type = other DNA
                        organism = synthetic construct
SEQUENCE: 44
aacgtagctt tc                                                            12

SEQ ID NO: 45           moltype = DNA  length = 12
FEATURE                 Location/Qualifiers
misc_feature            1..12
                        note = exemplary sequence
source                  1..12
                        mol_type = other DNA
                        organism = synthetic construct
SEQUENCE: 45
ctacgatgct ag                                                            12

SEQ ID NO: 46           moltype = DNA  length = 12
FEATURE                 Location/Qualifiers
misc_feature            1..12
                        note = exemplary sequence
source                  1..12
                        mol_type = other DNA
                        organism = synthetic construct
SEQUENCE: 46
gctcctatag aa                                                            12

SEQ ID NO: 47           moltype = DNA  length = 12
FEATURE                 Location/Qualifiers
misc_feature            1..12
                        note = exemplary sequence
source                  1..12
                        mol_type = other DNA
                        organism = synthetic construct
SEQUENCE: 47
tcggagacgc tg                                                            12

SEQ ID NO: 48           moltype = DNA  length = 12
FEATURE                 Location/Qualifiers
misc_feature            1..12
```

```
                             note = exemplary sequence
source                       1..12
                             mol_type = other DNA
                             organism = synthetic construct
SEQUENCE: 48
agcctagaat ct                                                              12

SEQ ID NO: 49                moltype = DNA  length = 12
FEATURE                      Location/Qualifiers
misc_feature                 1..12
                             note = exemplary sequence
source                       1..12
                             mol_type = other DNA
                             organism = synthetic construct
SEQUENCE: 49
tctgctacgt cg                                                              12

SEQ ID NO: 50                moltype = DNA  length = 12
FEATURE                      Location/Qualifiers
misc_feature                 1..12
                             note = exemplary sequence
source                       1..12
                             mol_type = other DNA
                             organism = synthetic construct
SEQUENCE: 50
tgctagaacg ta                                                              12

SEQ ID NO: 51                moltype = DNA  length = 12
FEATURE                      Location/Qualifiers
misc_feature                 1..12
                             note = exemplary sequence
source                       1..12
                             mol_type = other DNA
                             organism = synthetic construct
SEQUENCE: 51
ctacgatcgg ag                                                              12

SEQ ID NO: 52                moltype = DNA  length = 24
FEATURE                      Location/Qualifiers
misc_feature                 1..24
                             note = exemplary sequence
source                       1..24
                             mol_type = other DNA
                             organism = synthetic construct
SEQUENCE: 52
aacgtagctt tcctacgatg ctag                                                 24

SEQ ID NO: 53                moltype = DNA  length = 24
FEATURE                      Location/Qualifiers
misc_feature                 1..24
                             note = exemplary sequence
source                       1..24
                             mol_type = other DNA
                             organism = synthetic construct
SEQUENCE: 53
aacgtagctt tcctttctac gtag                                                 24
```

TARGETING CELL TROPISM RECEPTORS TO INHIBIT CYTOMEGALOVIRUS INFECTION

CLAIM OF PRIORITY

This application is a divisional of U.S. patent application Ser. No. 16/604,735, filed on Oct. 11, 2019, which is a U.S. National Stage Application under 35 USC § 371 of International Patent Application Serial No. PCT/US2018/027469, filed on Apr. 13, 2018, entitled "Targeting Cell Tropism Receptors to Inhibit Cytomegalovirus Infection," which claims the benefit of U.S. Provisional Patent Application Ser. No. 62/485,742, filed on Apr. 14, 2017. The entire contents of the foregoing are hereby incorporated by reference.

STATEMENT OF FEDERALLY SPONSORED RESEARCH

This invention was made with Government support under Grant No. AI109001 awarded by the National Institutes of Health. The Government has certain rights in the invention.

SEQUENCE LISTING

This application contains a Sequence Listing that has been submitted electronically as an XML file named "07917-0398002.XML." The XML file, created on Sep. 19, 2022, is 67,992 bytes in size. The material in the XML file is hereby incorporated by reference in its entirety.

TECHNICAL FIELD

Described herein are methods for treating or reducing the risk of a cytomegalovirus infection in a subject that include administering one or more of an inhibitor of Olfactory Receptor Family 14 Subfamily I Member 1 (OR14I1), an inhibitor of Deleted in Malignant Brain Tumors 1 (DMBT1), or an inhibitor of adenylyl cyclases.

BACKGROUND

Human cytomegalovirus (HCMV) is a major cause of morbidity and mortality in immunodeficient individuals, such as transplant patients, and is the leading cause of birth defects associated with congenital infection. There is no effective vaccine and therapeutic options are limited. Developing a vaccine that prevents HCMV infection or a therapy that treats or prevents HCMV-related disease are considered global health priorities.

SUMMARY

The present invention is based, at least in part, on the discovery of two host factors that are responsible for interactions with the pentameric complex and define epithelial tropism: OR14I1, a member of the olfactory receptor family, and DMBT1, a glycoprotein containing multiple scavenger receptor cysteine-rich (SRCR) domains separated by SRCR-interspersed domains (SID). As shown herein, targeting these proteins is effective in reducing viral entry and infection.

Thus, provided herein are methods for treating or reducing the risk of a cytomegalovirus (CMV) infection in a subject, e.g., a mammalian subject (such as a human subject). The methods include administering to the subject a therapeutically effective amount of one or more of an inhibitor of Deleted in Malignant Brain Tumors 1 (DMBT1), an inhibitor of Olfactory Receptor Family 14 Subfamily I Member 1 (OR14I1), or an inhibitor of adenylyl cyclases.

In some embodiments, the inhibitor of DMBT1 or inhibitor of OR14I1 is an antibody or antigen-binding fragment thereof, an inhibitory nucleic acid, a peptide that binds specifically to DMBT1 or OR14I1 (e.g., that blocks binding of the CMV to DMBT1 or OR14I1), or a peptide fragment of DMBT1 or OR14I1 (preferably a peptide fragment that binds to cytomegalovirus, e.g., to the CMV pentameric complex, and reduces entry of cytomegalovirus into a cell, e.g., an epithelial cell).

In some embodiments, the antibody or antigen binding fragment thereof is selected from the group consisting of monoclonal, recombinant, chimeric, de-immunized or humanized, fully human, non-human, and single chain antibodies.

In some embodiments, the inhibitor of OR14I1 is a N-terminal peptide of OR14I1 (e.g., that binds to cytomegalovirus and reduces entry of cytomegalovirus into a cell, e.g., an epithelial cell).

In some embodiments, the peptide comprises the amino acid sequence MDNLTKVTEFLLMEFSGIWELQVLHA (SEQ ID NO:1), or an active fragment thereof, e.g., as described herein.

In some embodiments, the inhibitor of adenylyl cyclases is selected from the group consisting of 9-Cyclopentyladenine monomethanesulfonate; 2',5'-Dideoxyadenosine; 2',5'-Dideoxyadenosine 3'-triphosphate tetrasodium salt; Dihomo-gamma-linolenylethanolamide; KH7; LRE1; MDL-12330A; NKY80; SB-268262; BPIPP; SKF 83566; and SQ 22,536.

In some embodiments, the inhibitory nucleic acid is selected from the group consisting of siRNA, shRNA, antisense, and a guide RNA/CRISPR Cas9 editing enzyme.

Also provided herein are inhibitors of DMBT1 or OR14I1 or adenylyl cyclase, and compositions, e.g., pharmaceutical compositions, comprising one or more of an inhibitor of Deleted in Malignant Brain Tumors 1 (DMBT1), an inhibitor of OR14I1, or an inhibitor of adenylyl cyclase, for use in a method of treating or reducing the risk of a cytomegalovirus infection in a subject.

In some embodiments, the inhibitor of DMBT1 or inhibitor of OR14I1 is an antibody or antigen-binding fragment thereof, an inhibitory nucleic acid, a peptide that binds specifically to DMBT1 or OR14I1 (e.g., that blocks binding of the CMV to CMBT1 or OR14I1), or a peptide fragment of DMBT1 or OR14I1 (preferably a peptide fragment that binds to cytomegalovirus, e.g., to the CMV pentameric complex, and reduces entry of cytomegalovirus into a cell, e.g., an epithelial cell). In some embodiments, the antibody or antigen binding fragment thereof is selected from the group consisting of monoclonal, recombinant, chimeric, de-immunized or humanized, fully human, non-human, and single chain antibodies. In some embodiments, the inhibitor of OR14I1 is a N-terminal peptide of OR14I1. In some embodiments, the peptide comprises the amino acid sequence MDNLTKVTEFLLMEFSGIWELQVLHA (SEQ ID NO:1), or an active fragment thereof, e.g., as described herein. In some embodiments, the inhibitor of adenylyl cyclases is selected from the group consisting of 9-Cyclopentyladenine monomethanesulfonate; 2',5'-Dideoxyadenosine; 2',5'-Dideoxyadenosine 3'-triphosphate tetrasodium salt; Dihomo-gamma-linolenylethanolamide; KH7; LRE1; MDL-12330A; NKY80; SB-268262; BPIPP; SKF 83566; and SQ 22,536.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

Figure 1:
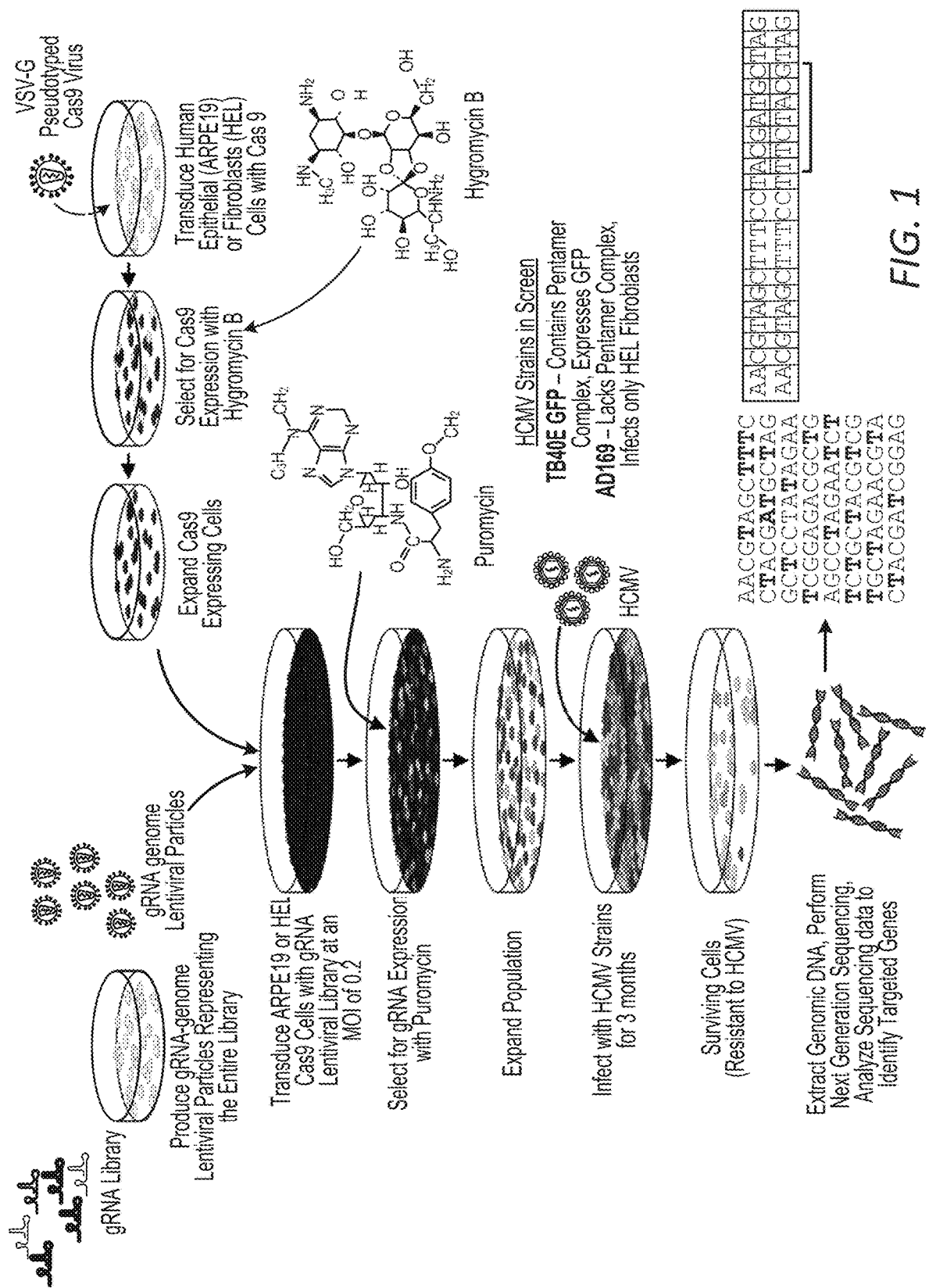
FIG. 1 is a schematic illustration of a genomic-wide CRISPR/Cas9 mediated screen used to identify host factors that are resistant to human cytomegalovirus (HCMV) replication. PCR, polymerase chain reaction. (SEQ ID NOs. 44-53, in order of appearance).

For the following figures, unless otherwise noted, all infections with HCMV were at an MOI=0.1 and cells processed at 48 hours post infection (hpi).

FIGS. 2A-I. OR14I1 and DMBT1 are required for HCMV infection of ARPE19 epithelial cells. (A) Resistance to HCMV TB40E-GFP strain infection in OR14I1, DMBT1 and PDGFRA deficient epithelial cells. (B) Western blots confirming the deficiency of OR14I1 and DMBT1 in the cells shown in (A); Actin western blots are included as loading controls. (C) Single clone derived, diploid knockout of OR14I1 cells were also resistant to TB40E-GFP infection. (D) HCMV infection resistance in PDGFRA deficient HEL fibroblasts, but not in OR14I1 or DMBT1 deficient HEL fibroblasts. (E) HCMV infection resistance in shOR14I1, shDMBT1 or shPDGFRA knock down cells. The shRNA knock down ARPE19 cells were infected with TB40E-GFP virus. (F) Flow cytometric analysis shows the GFP positive percentage after infection with TB40E-GFP. (G) Western blots to confirm the knockdown efficiency in (E) and (F). Actin is included as a loading control. (H) Resistance to CMV infection in shPDGFRA knockdown HEL fibroblasts, but not when shOR14I1 or shDMBT1 is knocked down in the same cell type. Fibroblasts were infected with HCMV strain Ad169. (I) Western blots confirm the depletion of PDGFRA and OR14I1 in (H). Actin is included as a loading control. Sg, SgRNA; sh, shRNA.

FIGS. 3A-J. Human OR14I1 and DMBT1 are required for optimal binding of HCMV TB40E-GFP to cells. (A) shPDGFRA, shOR14I1 and shDMBT1 transduced ARPE19 cells were infected with TB40E-GFP. The amount of viral DNA is represented as copies of the viral gene, UL83, per copy of the cellular gene, β-ACTIN. (B) The results in (A) are presented as the relative amount of reduction in viral DNA in the knock down cell lines relative to shCON. (C) shPDGFRA, shDMBT1 and shOR14I1 transduced ARPE19 cells were infected with TB40E-GFP, and internalized viral DNA levels were quantified by qPCR. (D) The results in (C) are presented as the relative amount of viral DNA in the knock down cell lines relative to shCON. (E) ARPE19-sgOR14I1 cells, ARPE19-sgOR14I1 cells rescued by transduction of a cDNA expressing OR14I1, and ARPE19-OR14I1 overexpressing cells were infected with TB40E-GFP and viral DNA levels were quantified by qPCR. Left panel, plot of qPCR results. Right panel, western blots of knockdown and rescue of OR14I1. Actin is included as a loading control. (F) Western blot showing the expression of flag-tagged human OR14I1 in Sf9 insect cells expressing human OR14I1 as detected by flag antibody. (G) Membrane flotation assay: TB40E virus was incubated with membrane vesicles from control Sf9 cells or Sf9 cells expressing human flag-OR14I1 (flag-OR). After centrifugation, fractions underwent immunoblotting to determine the levels of TB40E virus (viral protein pp65), and location of membrane vesicles (flag-OR14I1). (H), ARPE19 cells infected with TB40E-GFP or a PC-deleted TB40E-GFP (TB40EΔUL128-131, MOI=3.0). Cells were fixed at 2 dpi and assessed for GFP positive cells. (I), as in (A) using either TB40E-GFP or TB40EΔ UL128-131 virus (MOI=2.0). (J) TB40E-GFP virus was preincubated with Sf9-control or Sf9-flag-OR14I1 membrane vesicles prior to being used in a virus binding assay with ARPE19 cells (MOI=3.0). Viral (UL83) and cellular ((β-actin) DNA levels were quantified by qPCR. All data represent the mean of n=3 experiments+/−SD. $p<0.01$; *$p<0.001$; ****$p<0.0001$.

FIGS. 4A-H. OR14I1 bind to HCMV TB40E-GFP is dependent on virion pentamer complex proteins. (A) ARPE19 epithelial cell passaged TB40E (TB40E-ARPE19) virus expresses more pentamer complex and infects epithelial cells more effectively than HEL fibroblast passaged TB40E (TB40E-HEL) virus, which has reduced virion-associated pentamer complex. (B) Percentage infection of cells in (A). Values indicate the mean percent infected cells of 3 independent experiments±SD. (C) TB40E-ARPE19 virus have improved binding ability relative to TB40E-HEL virus; viral DNA levels were quantified by qPCR. (D), ARPE19 cells expressing the indicated sgRNAs were infected with TR5-GFP virus (TR5) or a TR5-GFP virus with the PC deleted (TR5ΔUL128-131, MOI=3.0). Cells were fixed at 2 dpi and imaged for GFP. The graph shows quantitation of data indicating the percent GFP positive cells. (E), Binding assay: ARPE19 cells were incubated with TR5 or TR5ΔUL128-131 for 1 hr on ice (MOI=2.0). After washing, cell-surface bound viral DNA (UL83) was quantified by qPCR and normalized to cellular DNA ((β-actin). (F), ARPE19 cells expressing the indicated sgRNAs were infected with either bacteria artificial chromosome-derived AD169 (BADwt) virus which lacks the PC, or UL131-repaired BAD virus (BADrUL131), which expresses the PC. Both viruses express GFP. Cells were fixed at 2 dpi and imaged for GFP and DNA. The graph shows quantitation of data indicating the percent GFP positive cells. (G), Binding assay: ARPE19 cells were incubated with either BADwt virus or BADrUL131 for 1 hr on ice (MOI=3.0). After washing, cell-surface bound viral DNA (UL83) was quantified by qPCR and normalized to cellular DNA ((β-actin). (H) Viral binding to human OR14I1 is blocked by HCMV neutralizing antibodies that target the viral pentamer complex, as shown by a membrane floating assay in which a control IgG antibody, anti-pUL128, or anti-pUL130, was preincubated with purified TB40E-GFP virus. All data represent the mean of n=3 experiments+/−SD. $p<0.01$; *$p<0.001$; ****$p<0.0001$.

FIGS. 5A-D. A human OR14I1 derived, N-terminal peptide, suppresses HCMV infection. (A) 3D prediction model of OR14I1 and the predicted positions of four peptides exposed to the cell surface. (B) Viral binding to ARPE19 cells in the presence of competing Sf9-OR14I1 membrane particles; viral DNA levels were quantified by qPCR. (C) An N-terminal peptide of OR14I1 can prevent HCMV infection of epithelial cells. Viral DNA levels were quantified by qPCR. (D) The results in (C) are presented as the relative amount of reduction in viral DNA relative to the controls. p<0.01; *p<0.001; ****p<0.0001.

FIGS. 6A-E. A synthetic peptide representing the N-terminus of OR14I1 (Peptide 1) was sufficient to prevent for TB40E-GFP virus binding ARPE19 cells. (A) Different amounts of peptide 1 were preincubated with TB40E-GFP virus and the mixture applied to ARPE19. Viral DNA levels were quantified by qPCR. (B) The results in (A) are presented as the relative amount of viral DNA relative to the DMSO control. (C) TB40E-GFP virus was preincubated with peptide 1 (100 µg/ml), or DMSO, followed by infection of ARPE19 cells (MOI=2.0). Cells were imaged for GFP expression at 2 dpi (D2) and 7 dpi (D7). (D) TB40E-GFP or BADrUL131-GFP virus, both expressing PC, were preincubated with peptide 1 (100 µg/ml), or DMSO prior to infection of ARPE19 cells (MOI=2.0). Cells were fixed and imaged for GFP at 2 dpi. All data represent the mean of n=3 experiments+/−SD. (E) Culture media supernatants from (C) were harvested on the indicated dpi and assayed for infectious virus by plaque assay. Values indicate the mean percent infected cells of 3 independent experiments±SD. ****p<0.0001.

Figure 7A:
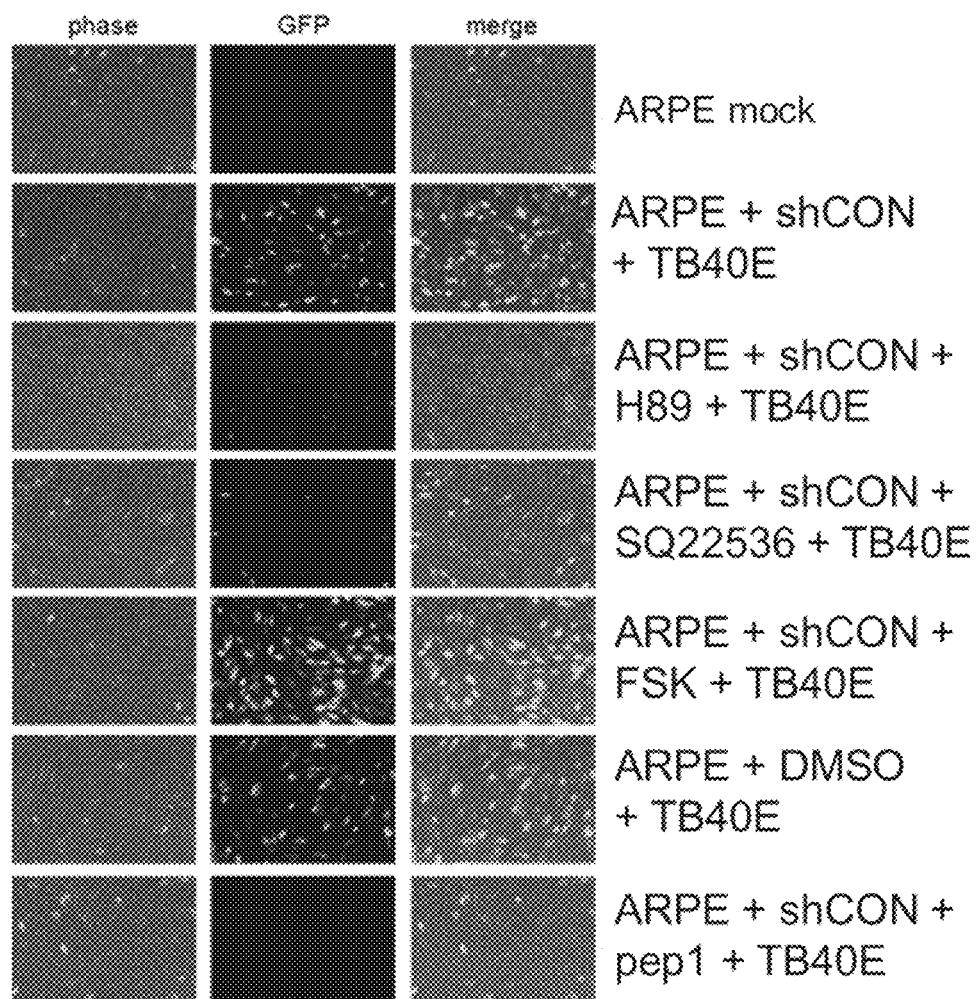
Figure 7B:
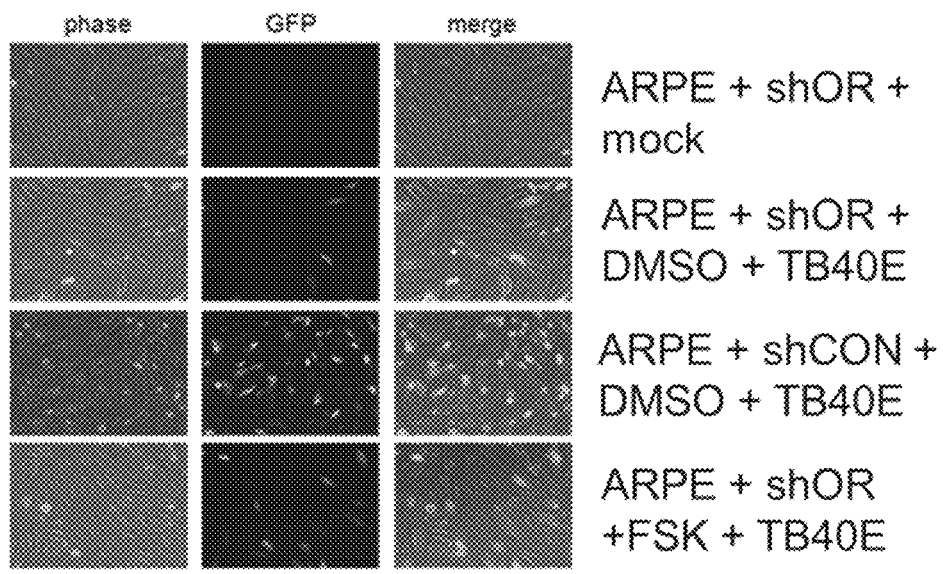
Figure 7C:
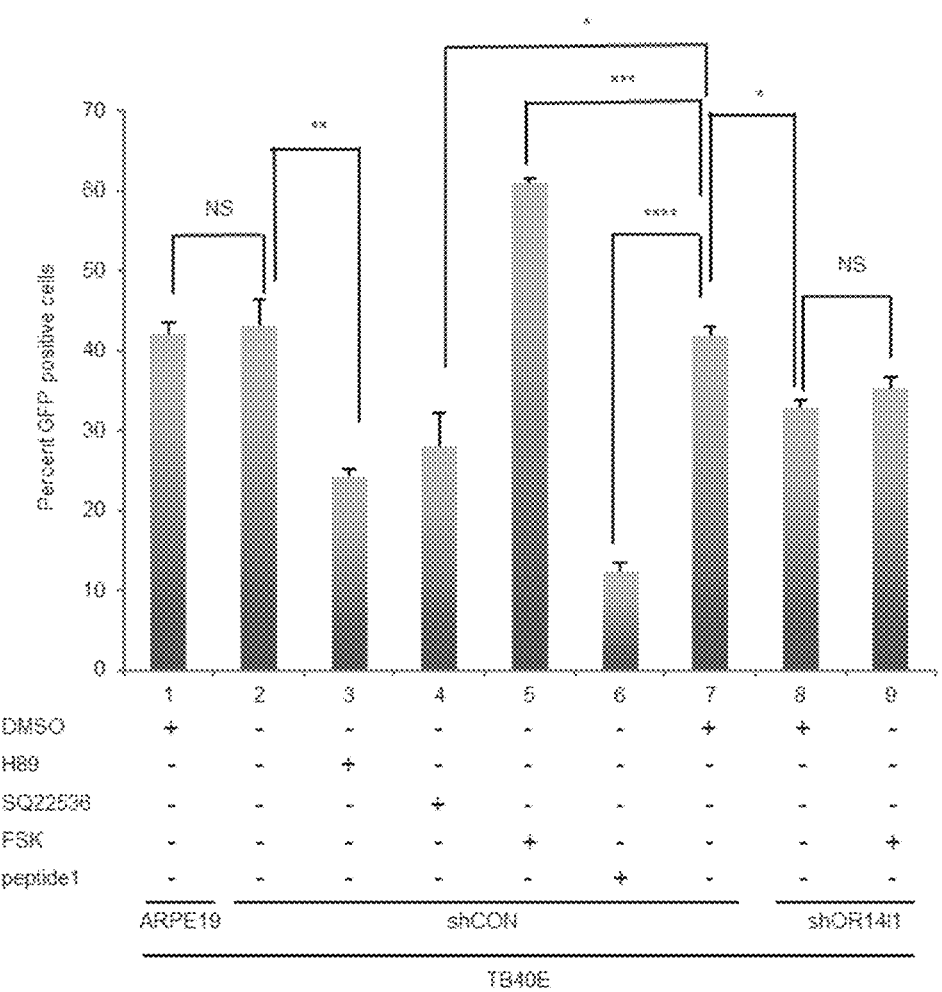

FIGS. 7A-C. HCMV receptor engagement and cAMP/PKA signaling. ARPE19 or OR14I1 knock down cells were pretreated with phosphokinase A (PKA) inhibitor H-89 (20 µM), adenylate cyclase antagonist, SQ22536 (150 µM), or adenylate cyclase activator, forskolin (FSK; 20 µM) for 2 h prior to TB40E-GFP infection (MOI=4.0). Cells were fixed at 48 hpi and images taken. Data quantified is shown in FIG. 7C.

Figure 8A:
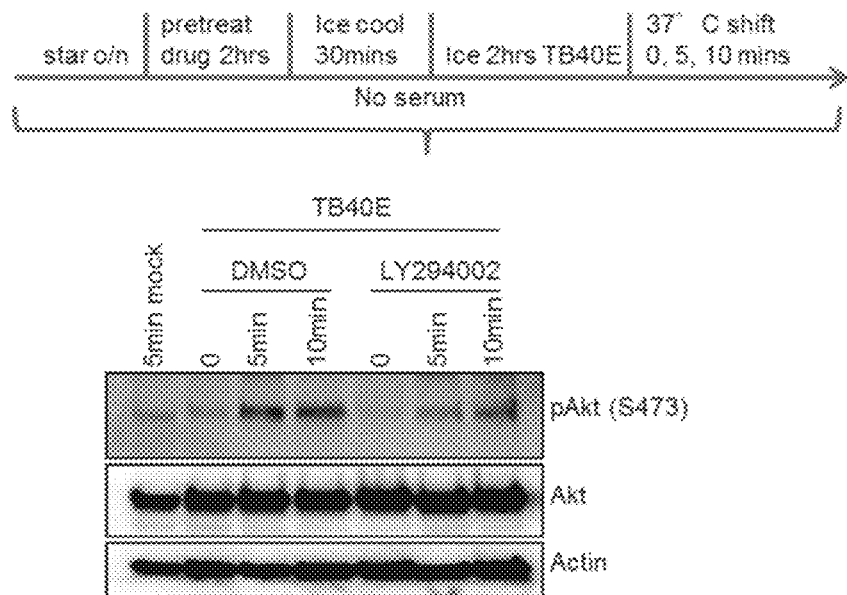
Figure 8B:
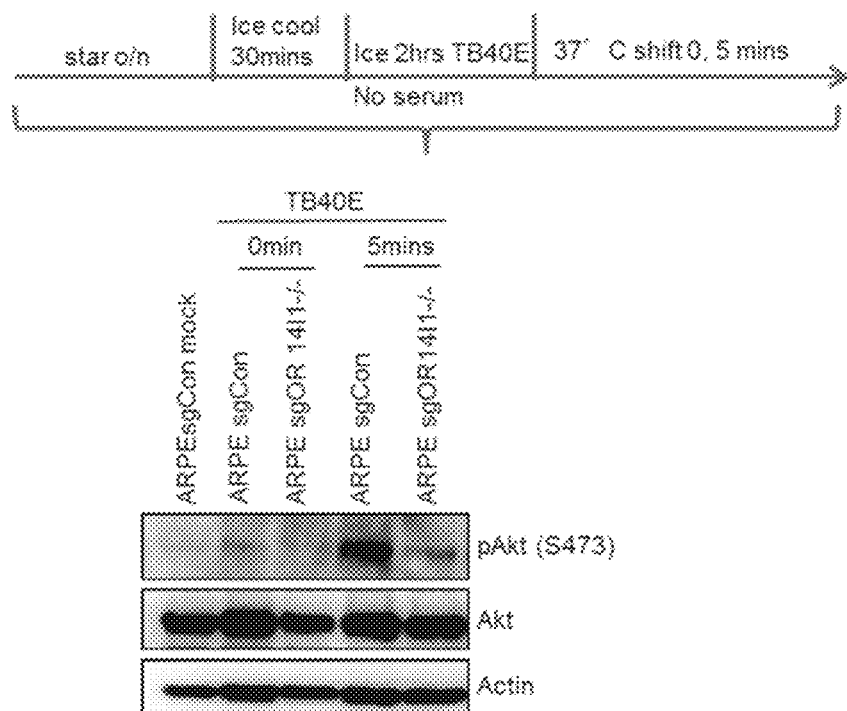
Figure 8C:
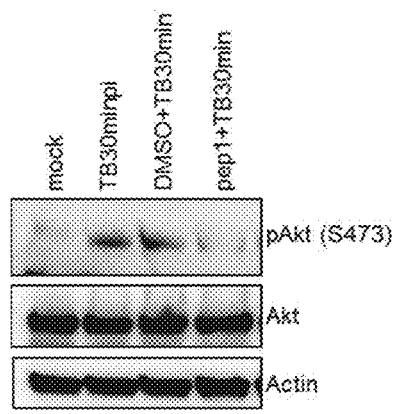

FIGS. 8A-C. Akt signaling rapidly induced by TB40E depends on OR14I1. (A) Cells were serum starved at 37° C. for overnight and cells were pretreated with DMSO (control), LY294002 (50 uM) in serum-free medium prior to infection for two hours. Plated cells were cooled on ice for 30 mins. Cells were infected by purified TB40E-GFP virus (no serum) at MOI of 2.0 PFU per cell for 2 hours on ice. Cell plates were then shifted to 37° C. incubator (time 0). Cells were harvested at 0, 5, 10 mins post infection. Protein extracts were subjected to immunoblotting with anti-phospho Akt (ser473), Akt or anti-β-actin (loading control). (B) ARPE19 epithelial sgCon and sgOR14I1 knock out cells were serum starved at 37° C. for overnight. Plated cells were cooled on ice for 30 mins. Cells were infected by purified TB40E-GFP virus (no serum) at MOI of 2.0 PFU per cell for 2 hours on ice. Cell plates were then shifted to 37° C. incubator (time 0). Cell were harvested at 0, 5 mins post infection. (C) Peptide 1 (100 ug/ml) was preincubated with TB40E-GFP virus at 37° C. for 2 h and the mixture applied to ARPE19 cells. The phosphorylation of Akt and total Akt were detected 30 minutes post infection of TB40E-GFP.

Figure 9:
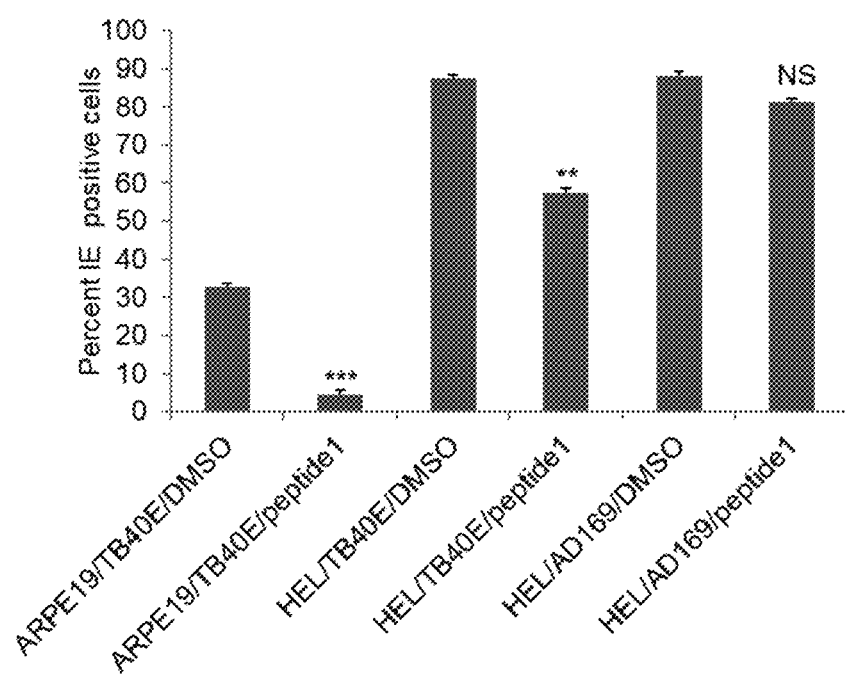

FIG. 9. An N-terminal peptide of OR14I1 blocks HCMV infection of ARPE19 epithelial cells and is dependent on the presence of viral PC. TB40E-GFP encoding the viral PC or AD169 lacking PC were preincubated with peptide 1 (100 µg/ml) and then infected on ARPE19 epithelial cells or HEL fibroblasts (MOI=2.0). Cells were fixed, permeabilized, stained for DNA, immunostained for anti-immediate early protein (IE) and imaged. The graph shows the results of quantitation of data indicating the percent IE positive cells. Values indicate the mean percentage of infected cells of n=3 experiments±SD. p<0.01; *p<0.001.

Figure 10:
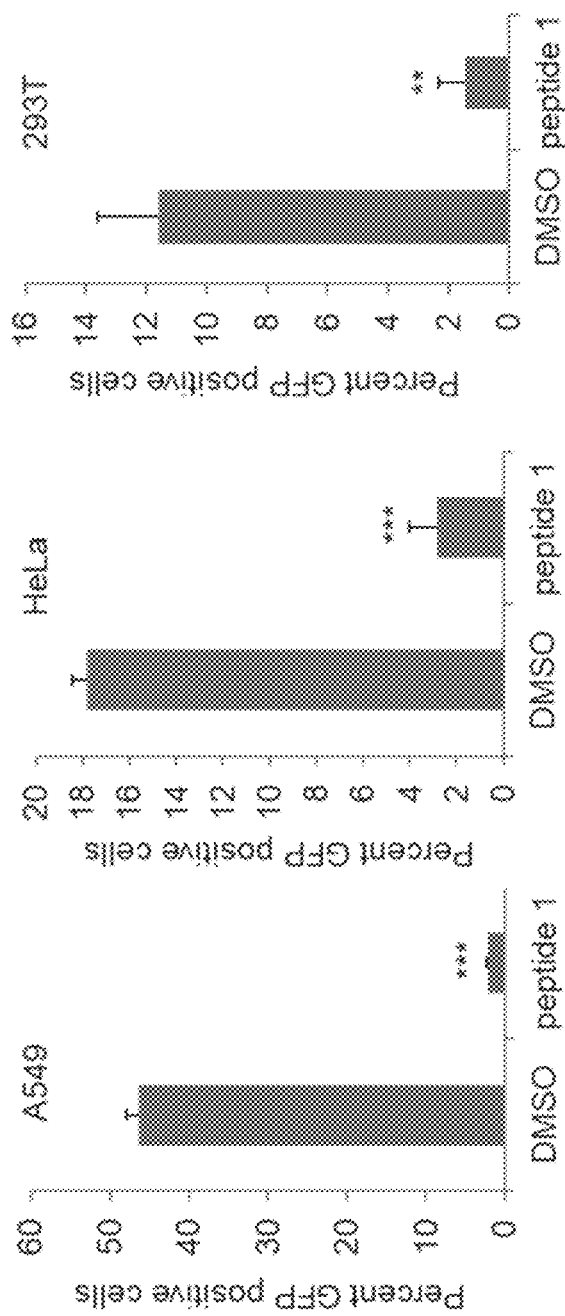

FIG. 10. N-terminal peptide of OR14I1 inhibits HCMV infection of several epithelial cell lines. Peptide 1 (100 µg/ml), or DMSO alone was preincubated with TB40E virus, followed by infection of the indicated epithelial cell lines (MOI=2.0). Cells were fixed and imaged for GFP and DNA at 2 dpi. The graph shows the results of quantitation of data indicating the percent GFP positive cells. Values indicate the mean percentage of infected cells of three experiments±SD. p<0.01; *p<0.001.

Figure 11:
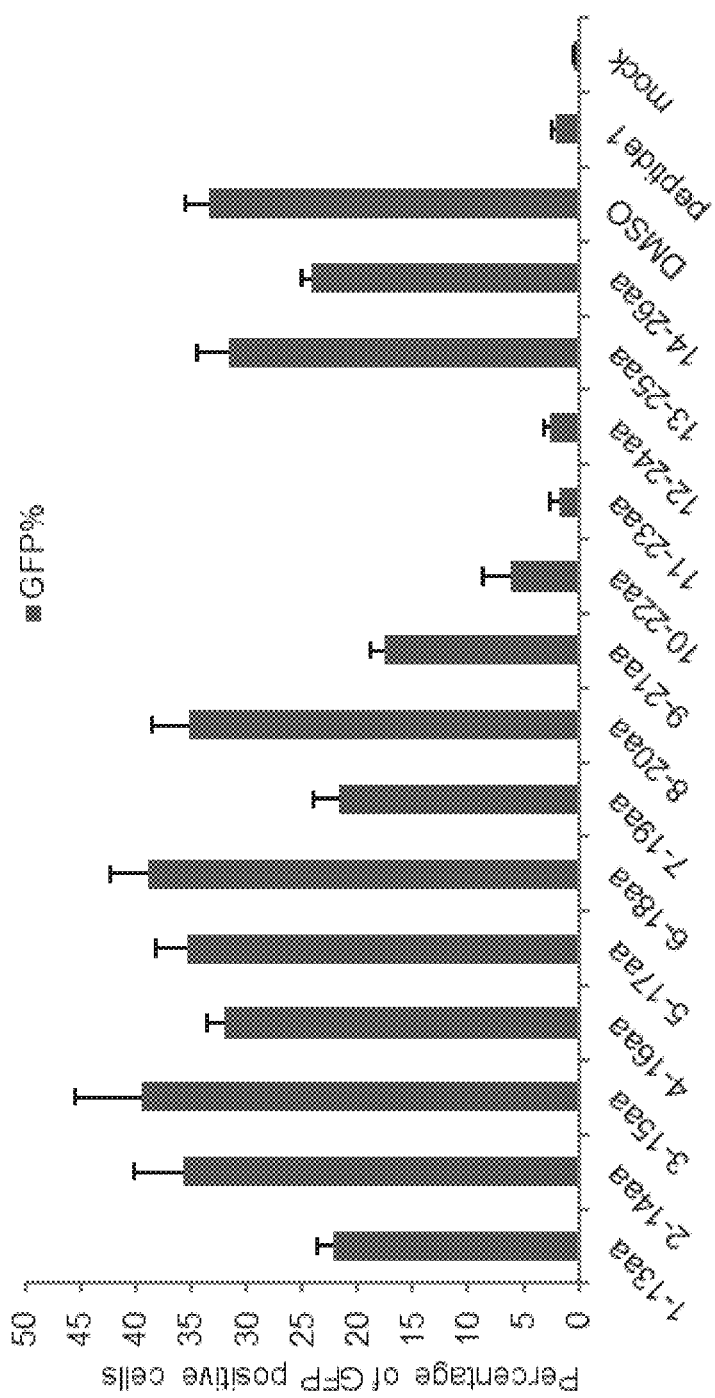

FIG. 11. Each of the short peptides (aa sequences listed in Table 4; 150 uM), Peptide 1 (32.6 µM), or DMSO alone was preincubated with TB40E virus, followed by infection of ARPE19 cell lines (MOI=2.0). Cells were fixed and imaged for GFP and DNA at 2 dpi. Quantitation data indicating the percent GFP positive cells.

DETAILED DESCRIPTION

HCMV is a member of the Herpesviridae family of viruses. HCMV is an enveloped beta-herpesvirus with an approximately 235 kb double-stranded DNA genome containing approximately 200 open reading frames (ORFs). The HCMV genome is divided into two segments, designated UL (unique long) and US (unique short), bounded by inverted repeats.

A HCMV "pentameric" glycoprotein complex (gH, gL, UL128, UL130, and UL131A) is responsible for tropism for clinically relevant cell types including infection of epithelial cells (Wang et al., Proc Natl Acad Sci USA 2005, 102 (50): 18153-8; Adler et al., J Gen Virol 2006, 87: 2451-60; Ryckman et al., J Virol 2006, 80: 710-22; Ryckman et al., Proc Natl Acad Sci USA 2008, 105: 14118-23). HCMV neutralizing antibodies that target this pentameric complex are useful to limit HCMV infection (Wang et al., Proc Natl Acad Sci USA 2005, 102 (50): 18153-8). As such, current vaccine and immunotherapeutic approaches focus on creating immune responses to this complex (Chiuppesi et al., J Virol 2015, 89 (23): 11884-98). No cellular receptor has been identified that interacts with the pentameric complex. Here, a genome-wide CRISPR/Cas9-based screen was performed to identify host genes that, when edited, resulted in reduced HCMV infection (Tao et al., Nature 2016, 538: 350-5; Savidis et al., Cell Rep 2016, 16: 232-46; Perreira et al Adv Virus Res 2016, 94: 1-51; Shalem et al., Science 2014, 343: 84-7). Two host factors responsible for interactions with the pentameric complex that define epithelial tropism were identified and validated. OR14I1 is a member of the olfactory receptor family. DMBT1 is a glycoprotein containing multiple scavenger receptor cysteine-rich (SRCR) domains separated by SRCR-interspersed domains (SID). Loss of OR14I1 or DMBT1 expression markedly reduced entry of HCMV into epithelial cells but not fibroblasts. Pentameric complex-targeted neutralizing antibodies prevent binding of HCMV to OR14I1. Exogenously expressed human OR14I1 protein or a synthetic peptide based on the predicted OR14I1 protein sequence effectively blocks HCMV entry and prevent the initial activation of AKT signaling induced by CMV. G-protein coupled receptors (GPCR) such as OR14I1 signal through the generation of cAMP by adenylylcyclases (Miazzi et al., J Exp Biol 2016, 219 (Pt 12): 1798-803). Consistent with this principle, HCMV infection of epithelial cells was also prevented by inhibitors of adenylyl cyclases. The identification of OR14I1 and a downstream signaling pathway improves our understanding of the pathogenesis of infection and provides a target for the development of novel antiviral interventions.

Methods of Treatment

Provided herein are prophylactic and therapeutic methods for treating a subject at risk of (or susceptible to) or a subject having a virus (e.g., CMV virus, e.g., HCMV) that include administration of an agent that targets or inhibits OR14I1 or DMBT1, e.g., an inhibitory fragment of OR14I1 or DMBT1, an antibody or inhibitory nucleic acid or peptide, and/or an inhibitor of adenylyl cyclases. "Treatment", or "treating" as used herein, is defined as the application or administration of a therapeutic agent as described herein to a patient, or application or administration of a therapeutic agent to an isolated tissue or cell line from a patient, who has a virus with the purpose to cure, heal, alleviate, relieve, alter, remedy, ameliorate, improve or affect the virus, or symptoms of the virus. The term "treatment" or "treating" is also used herein in the context of administering agents prophylactically, e.g., to inoculate against a virus.

In one aspect, the invention provides a method for reducing risk of infection with or transmission of the CMV (e.g., HCMV) virus or a condition associated with the CMV virus, e.g., non-Epstein-Barr virus infectious mononucleosis, pneumonia, colitis, esophagitis, hepatitis, central nervous system (CNS) disease including encephalitis and polyradiculitis; leukopenia, adrenalitis and oral ulcers (particularly in persons with AIDS); neurological problems including deafness in congenitally infected children; encephalitis; Lumbosacral Polyradiculopathy and Myelitis; Mononeuritis Multiplex; retinitis; CMV-associated gastrointestinal disease; and CMV-associated malignancies including breast cancer and glioblastoma (Demmler et al., Rev Infect Dis 1991, 13: 315-29; Istas et al., Clin Infect Dis 1995, 20: 665-70; Uziel et al., Harefuah 1991, 120: 536-9; Malinger et al., AJNR Am J Neuroradiol 2003, 24: 28-32), by administering to the subject a prophylactically effective agent as described herein. Administration of a prophylactic agent can occur prior to the manifestation of symptoms characteristic of CMV infection, such that CMV infection and/or CMV related diseases are prevented.

In some embodiments, the prophylactically effective agent is administered to the subject prior to exposure to the CMV virus. In another embodiment, the agent is administered to the subject after exposure to the CMV virus to delay or inhibit its progression. Thus, the method is prophylactic in the sense that healthy cells are protected from CMV infection. The methods generally include administering the agent to the subject such that CMV infection is prevented or inhibited.

The present methods can also be used for therapeutic purposes, e.g., by contacting a cell infected with the virus with a therapeutic agent (e.g., a siRNA or vector or transgene encoding same) that is specific for a portion of the viral genome such that RNAi is mediated. These methods can be performed ex vivo (e.g., by culturing a cell or contacting a tissue with the agent, e.g., a tissue that is to be transplanted into an individual) or, alternatively, in vivo (e.g., by administering the agent to a subject). The methods can be performed ex vivo and then the products introduced to a subject (e.g., gene therapy).

Adenylyl Cyclase

Adenylyl Cyclase (or Adenylate Cyclase) enzymes catalyze conversion of adenosine triphosphate (ATP) to cyclic adenosine monophosphate (cAMP). A number of inhibitors of adenylyl cyclase are known in the art, including 9-Cyclopentyladenine monomethanesulfonate; 2',5'-Dideoxyadenosine; 2',5'-Dideoxyadenosine 3'-triphosphate tetrasodium salt; Dihomo-gamma-linolenylethanolamide; KH7 ((±)-2-(1H-benzimidazol-2-ylthio)propanoic acid 2-[(5-bromo-2-hydroxyphenyl)methylene]hydrazide); LRE1 (6-Chloro-N4-cyclopropyl-N4-(2-thienylmethyl)-2,4-pyrimidinediamine, RU-0204277); MDL-12330A ((±)-N-[(1R*,2R*)-2-Phenylcyclopentyl]-azacyclotridec-1-en-2-amine hydrochloride); NKY80 (2-Amino-7-(2-furanyl)-7,8-dihydro-5(6H)-quinazolinone); SB-268262 (N-Methyl-N-(2-methylphenyl)-3-nitro-4-(2-thiazolylsulfinyl)-benzamide); BPIPP (5-(3-Bromophenyl)-5,11-dihydro-1,3-dimethyl-1H-indeno[2',1':5,6]pyrido[2,3-d]pyrimidine-2,4,6(3H)-trione; Kots et al., Proc. Natl. Acad. Sci. USA 105 8440); SKF 83566 (8-Bromo-2,3,4,5-tetrahydro-3-methyl-5-phenyl-1H-3-benzazepin-7-ol hydrobromide); and SQ 22,536 (9-(Tetrahydro-2-furanyl)-9H-purin-6-amine), all of which are commercially available. Certain forskolin analogs are also inhibitory, see Pinto et al., JPET 325:27-36, 2008.

OR14I1

OR14I1 is an olfactory receptor protein, a member of a large family of G-protein-coupled receptors (GPCR) that share a 7-transmembrane domain structure with many neurotransmitter and hormone receptors.

An exemplary sequence of human OR14I1 mRNA is as follows (from NCBI RefSeq ID NM_001004734.1):

SEQ ID NO: 43

```
  1 atggacaatc tcacaaaagt gacagaattc ctgctgatgg agttttctgg tatctgggag 61 ctgcaggtgc tgcacgccgg gctgtttctg ctgatttatc tggcagtgct ggtggggaac 121 ctgctcatca ttgcagtcat cactctcgat cagcatcttc acacacccat gtacttcttc 181 ctgaagaacc tctccgtttt ggatctgtgc tacatctcag tcactgtgcc taaatccatc 241 cgtaactccc tgactcgcag aagctccatc tcttatcttg gctgtgtggc tcaagtctat 301 tttttctctg cctttgcatc tgctgagctg gccttcctta ctgtcatgtc ttatgaccgc 361 tatgttgcca tttgccaccc cctccaatac agagccgtga tgacatcagg agggtgctat 421 cagatggcag tcaccacctg gctaagctgc tttttcctacg cagccgtcca cactggcaac 481 atgtttcggg agcacgtttg cagatccagt gtgatccacc agttcttccg tgacatccct 541 catgtgttgg ccctggtttc ctgtgaggtt ttctttgtag agttttttgac cctggccctg 601 agctcatgct tggttctggg atgctttatt ctcatgatga tctcctattt ccaaatcttc 661 tcaacggtgc tcagaatccc ttcaggacag agtcgagcaa aagccttctc cacctgctcc 721 ccccagctca ttgtcatcat gctctttctt accacagggc tctttgctgc cttaggacca
```

-continued

```
781 attgcaaaag ctctgtccat tcaggattta gtgattgctc tgacatacac agttttgcct 841 cccttcctca atcccatcat atatagtctt aggaataagg agattaaaac agccatgtgg 901 agactctttg tgaagatata ttttctgcaa aagtag
```

An exemplary sequence of human OR14I1 protein is as follows (from NCBI RefSeq ID NP_001004734.1):

SEQ ID NO: 2

```
  1 mdnltkvtef llmefsgiwe iqvlhaglfl liylavlvgn lliiavitld qhlhtpmyff 61 iknlsvldlc yisvtvpksi rnsltrrssi sylgcvaqvy ffsafasael afltvmsydr 121 yvaichplqy ravmtsggcy qmavttwlsc fsyaavhtgn mfrehvcrss vihqffrdip 181 hvlalvscev ffvefltlal ssclvlgcfi lmmisyfqif stvlripsgq srakafstcs 241 pqlivimlfl ttglfaalgp iakalsiqdl vialtytvlp pflnpiiysl rnkeiktamw 301 rlfvkiyflq k
```

Deleted in Malignant Brain Tumors 1 (DMBT1)

DMBT1 is a glycoprotein with multiple scavenger receptor cysteine-rich (SRCR) domains separated by SRCR-interspersed domains (SID). DMBT1 may play a role in the interaction of tumor cells and the immune system.

Exemplary sequences of human DMBT1 are provided in Table 1.

TABLE 1

| Transcript variant | NCBI RefSeq ID | Isoform | NCBI RefSeq ID |
|---|---|---|---|
| Variant 1 | NM_004406.2 | Isoform a precursor | NP_004397.2 |
| Variant 2 | NM_007329.2 | Isoform b precursor | NP_015568.2 |
| Variant 3 | NM_017579.2 | Isoform c precursor | NP_060049.2 |
| Variant 4 | NM_001320644.1 | Isoform d precursor | NP_001307573.1 |

Each of the above sequences is incorporated by reference herein.

Antibodies

The methods described herein can include the use of antibodies to an OR14I1 or DMBT1 protein. The term "antibody" as used herein refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, *Antibodies: A Laboratory Manual* (1988); Goding, *Monoclonal Antibodies: Principles and Practice*, (N.Y. Academic Press 1983); Howard and Kaser, *Making and Using Antibodies: A Practical Handbook* (CRC Press; 1st edition, Dec. 13, 2006); Kontermann and Dübel, *Antibody Engineering Volume 1* (*Springer Protocols*) (Springer; 2nd ed., May 21, 2010); Lo, *Antibody Engineering: Methods and Protocols* (*Methods in Molecular Biology*) (Humana Press; Nov. 10, 2010); and Dübel, *Handbook of Therapeutic Antibodies: Technologies, Emerging Developments and Approved Therapeutics*, (Wiley-VCH; 1 edition Sep. 7, 2010). Antibodies useful in the present methods include those that bind specifically to (i.e., do not bind to targets other than) OR14I1 or DMBT1, and that inhibit cellular engagement with CMV and/or reduce adenylate cyclase signaling, and block infection of mammalian epithelial cells, e.g., as shown herein.

In some embodiments, the antibody can be coupled to a detectable or imaging agent. Such agents are well known in the art and include paramagnetic agents, bioluminescent or fluorescent labels (e.g., GFP, FITC, rhodamine, or Texas Red), radioactive isotopes, and colorimetric/enzymatic agents (e.g., HRP, B-galactosidase). In a preferred embodiment, the antibody is coupled to a paramagnetic agent, e.g., a paramagnetic nanoparticle, e.g., cross-linked iron oxide (CLIO) nanoparticles; see, e.g., US 20110046004; Josephson et al., Bioconjug. Chem., 10(2):186-91 (1999).

Peptides

In some embodiments, an inhibitor of OR14I1 comprises a peptide comprising all or a part of the N-terminus of OR14I1. Exemplary peptides can comprise Peptide 1, or a peptide as shown in Table 4, or a peptide comprising amino acids FLLMEFSGIWELQ (SEQ ID NO:3), LLMEFSGIWELQV (SEQ ID NO:4), or LMEFSGIWELQVL (SEQ ID NO:5), or LMEFSGIWELQ (SEQ ID NO:6). The peptides can be made using methods known in the art, e.g., using known chemical peptide synthesis or recombinant methods using expression in a host cell.

In some embodiments, the peptides disclosed herein can be modified according to the methods known in the art for producing peptidomimetics. See, e.g., Kazmierski, W. M., ed., Peptidomimetics Protocols, Human Press (Totowa NJ 1998); Goodman et al., eds., Houben-Weyl Methods of Organic Chemistry: Synthesis of Peptides and Peptidomimetics, Thiele Verlag (New York 2003); and Mayo et al., J. Biol. Chem., 278:45746 (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N terminus to the C terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetic include replacing one or more amino acid residues in a peptide with a chemically distinct but recognized functional analog of the amino acid, i.e., an artificial amino acid analog. Artificial amino acid analogs include beta-amino acids, beta-substituted beta-amino acids ("beta3-amino acids"), phosphorous analogs of amino acids, such as a-amino phosphonic acids and b-amino phosphinic acids, and amino acids having non-peptide linkages. Artificial amino acids can be used to create peptidomimetics, such as peptoid oligomers (e.g., peptoid amide or ester analogues), beta-peptides, cyclic peptides, oligourea or oligocarbamate peptides; or heterocyclic ring molecules. Exemplary retro-inverso peptidomimetics can comprise the sequence QLEWIGSFEML (SEQ ID NO:7), preferably wherein the sequence includes all D-amino acids.

The peptide sequences described herein can be modified, e.g., by modification of one or more amino acid residues of a peptide by chemical means, either with or without an enzyme, e.g., by alkylation, acylation, ester formation, amide formation, e.g., at the carboxy terminus, or biotinylation, e.g., of the amino terminus. In some embodiments, the peptides are modified by the addition of a lipophilic substituent (e.g., a fatty acid) to an amino acid, e.g., to a Lysine. In some embodiments, the peptides include one or more of an N-terminal imidazole group, or a C-terminal amide group. In some embodiments, the epsilon-amino group of Lys34 is substituted with a lipophilic substituent, e.g., of about 4-40 carbon atoms, e.g., 8-25 carbon atoms. Examples include branched and unbranched C6-C20 acyl groups. Exemplary lipophilic substituents, and methods of attaching the same (including via an optional linker) are provided in U.S. Pat. No. 6,268,343 and Knudsen et al., J. Med. Chem. 43:1664-1669 (2000). In some embodiments, the lipophilic substituent is a fatty acid selected from the group consisting of straight-chain or branched fatty acids, e.g., oleic acid, caprylic acid, palmitic acid, and salts thereof.

In some embodiments, the peptide sequences are modified by substituting one or more amino acid residues of the parent peptide with another amino acid residue. In some embodiments, the total number of different amino acids between the sequence-modified peptide and the corresponding native form of the peptide is up to five, e.g., up to four amino acid residues, up to three amino acid residues, up to two amino acid residues, or one amino acid residue.

In some embodiments, the total number of different amino acids does not exceed four. In some embodiments, the number of different amino acids is three, two, or one. In order to determine the number of different amino acids, one should compare the amino acid sequence of the sequence-modified peptide derivative with the corresponding native fragment.

Nucleic Acids, Vectors, and Host Cells

In one aspect, the invention includes nucleic acids encoding a peptide or modified peptide as described herein. For example, the invention includes nucleic acids encoding peptides that include a sequence set forth herein, e.g., the sequence SEQ ID NO:1 or a portion thereof. Nucleic acids disclosed herein also include nucleic acids encoding certain modified peptides, e.g., retro-peptides, peptides linked to a cellular internalization (carrier) sequence, and peptides linked to a carrier sequence.

Nucleic acids disclosed herein also include both RNA and DNA, including genomic DNA and synthetic (e.g., chemically synthesized) DNA. Nucleic acids can be double-stranded or single-stranded. Nucleic acids can be synthesized using oligonucleotide analogs or derivatives (e.g., inosine or phosphorothioate nucleotides). Such oligonucleotides can be used, for example, to prepare nucleic acids with increased resistance to nucleases.

Also included in the invention are genetic constructs (e.g., vectors and plasmids) that include a nucleic acid encoding a peptide described herein operably linked to a transcription and/or translation sequence that enables expression of the peptide, e.g., expression vectors. A selected nucleic acid, e.g., a DNA molecule encoding a peptide described herein, is "operably linked" to another nucleic acid molecule, e.g., a promoter, when it is positioned either adjacent to the other molecule or in the same or other location such that the other molecule can direct transcription and/or translation of the selected nucleic acid.

Also included in the invention are various engineered cells, e.g., transformed host cells, which contain a nucleic acid disclosed herein. A transformed cell is a cell into which (or into an ancestor of which) has been introduced, by means of recombinant DNA techniques, a nucleic acid encoding a peptide described herein that inhibits infection. Both prokaryotic and eukaryotic cells, e.g., mammalian cells (e.g., tumor cell), yeast, fungi, and bacteria (such as *Escherichia coli*), can be host cells. An engineered cell exemplary of the type included in the invention is a mammalian, bacterial, or insect cell that expresses a peptide described herein.

Inhibitory Nucleic Acids

Inhibitory nucleic acids useful in the present methods and compositions include antisense oligonucleotides, ribozymes, external guide sequence (EGS) oligonucleotides, guide RNA/CRISPR Cas9, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics which hybridize to at least a portion of the target OR14I1 or DMBT1 nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the OR14I1 or DMBT1 sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively, or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within an OR14I1 or DMBT1 sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general, the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

siRNA/shRNA

In some embodiments, the nucleic acid sequence that is complementary to an OR14I1 or DMBT1 RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general, the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 rnM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

CRISPR

The present methods can also include introducing a mutation(s) or a deletion(s) into an endogenous locus. In some embodiments of any of the methods described herein, DMBT1 or OR14I1 expression may be altered or lost by using techniques known in the art to disrupt the endogenous gene locus. Non-limiting examples of such techniques include: site-directed mutagenesis, CRISPR (e.g., CRISPR/Cas9-induced knock-in mutations, or CRISPR/Cas9-induced knock-out mutations), or TALENs. Skilled practitioners will appreciate that the nucleic acids and expression vectors described herein can be introduced into any subject (e.g., introduced into any cell of a subject), for example, by lipofection, or CRISPR, and can be stably integrated into an endogenous gene locus.

As used herein, "Clustered regularly interspaced short palindromic repeats" or "CRISPR" refers to a two component ribonucleoprotein complex with a Cas9 nuclease and a guide RNA. Bacteria and archaea used this system to detect and silence foreign nucleic acids in a sequence-specific manner (Jinek et al. Science 2012; 337(6096): 816-21). Methods of how to make and use CRISPR/Cas9 constructs are widely available and known by those skilled in the art, e.g., Cho et al., Nature Biotech. 2013; 31: 230-232; Cong et al., Science 2013; 339(6121): 819-23; Hwang et al., Nature Biotech. 2013; 31(3): 227-9; Jiang et al., Nature Biotech. 2013; 31(3): 233-9; and Mali et al., Science 2013; 339 (6121): 823-6.

The present methods can include the delivery of nucleic acids encoding a CRISPR DMBT1 or OR14I1 gene editing complex. The gene editing complex includes a Cas9 editing enzyme and one or more guide RNAs directing the editing enzyme to DMBT1 or OR14I1. In some embodiments, the methods can include using a plurality of guide RNAs that direct the editing enzyme to both DMBT1 and OR14I1.

The guide RNAs directing the editing enzyme to one or both of DMBT1 or OR14I1 comprise a sequence that is complementary to the sequence of a nucleic acid encoding DMBT1 or OR14I1, and that include a PAM sequence that is targetable by the co-administered Cas9 editing enzyme. In some embodiments the guide RNA comprises a sequence that is complementary to the sequence of a nucleic acid encoding DMBT1 (e.g., NCBI RefSeqGene No. NG_012644.1) or OR14I1 (e.g., NCBI Acc. No. NC_018912.2 Alternate CHM1_1.1 or NC_000001.11 (Chr. 1, nts 248681296-248685566, complement; GRCh38.p7)).

Cas9 Editing Enzymes

The methods include the delivery of Cas9 editing enzymes to the cancer cells. A number of Cas9s from various species can be used, including those shown in Table A. Suitable target sequences for use with those Cas9s can readily be determined using known methods.

TABLE A

Additional Cas9s from various species

| Species/Variant of Cas9 | PAM Sequence |
|---|---|
| SpCas9 D1135E variant | NGG (reduced NAG binding) |
| SpCas9 VRER variant | NGCG |
| SpCas9 EQR variant | NGAG |
| SpCas9 VQR variant | NGAN or NGNG |
| Streptococcus thermophilus (ST) | NNAGAAW |
| Treponema denticola (TD) | NAAAAC |
| Streptococcus pyogenes (SP); SpCas9 | NGG |
| Staphylococcus aureus (SA); SaCas9 | NNGRRT or NNGRR(N) |
| Neisseria meningitidis (NM) | NNNNGATT |

The editing enzymes can include one or more of SpCas9 D1135E variant; SpCas9 VRER variant; SpCas9 EQR variant; SpCas9 VQR variant; *Streptococcus thermophilus* (ST) Cas9 (StCas9); *Treponema denticola* (TD) (TdCas9); *Streptococcus pyogenes* (SP) (SpCas9); *Staphylococcus aureus* (SA) Cas9 (SaCas9); or *Neisseria meningitidis* (NM) Cas9 (NmCas9), as well as variants thereof that are at least 80%, 85%, 90%, 95%, 99% or 100% identical thereto that retain at least one function of the parent case, e.g., the ability to complex with a gRNA, bind to target DNA specified by the gRNA, and alter the sequence of the target DNA.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

The PAM sequences of these Cas9s are listed in Table D, above. The sequences of the Cas9s are known in the art; see, e.g., Kleinstiver et al., Nature. 2015 Jul. 23; 523(7561): 481-485; WO 2016/141224; U.S. Pat. No. 9,512,446; US-2014-0295557; WO 2014/204578; and WO 2014/144761. The methods can also include the use of the other previously described variants of the SpCas9 platform (e.g., truncated sgRNAs (Tsai et al., Nat Biotechnol 33, 187-197 (2015); Fu et al., Nat Biotechnol 32, 279-284 (2014)), nickase mutations (Mali et al., Nat Biotechnol 31, 833-838 (2013); Ran et al., Cell 154, 1380-1389 (2013)), FokI-dCas9 fusions (Guilinger et al., Nat Biotechnol 32, 577-582 (2014); Tsai et al., Nat Biotechnol 32, 569-576 (2014); WO2014144288).

See also Hou, Z. et al. Efficient genome engineering in human pluripotent stem cells using Cas9 from *Neisseria meningitidis*. Proc Natl Acad Sci USA (2013); Fonfara, I. et al. Phylogeny of Cas9 determines functional exchangeability of dual-RNA and Cas9 among orthologous type II CRISPR-Cas systems. Nucleic Acids Res 42, 2577-2590 (2014); Esvelt, K. M. et al. Orthogonal Cas9 proteins for RNA-guided gene regulation and editing. Nat Methods 10, 1116-1121 (2013); Cong, L. et al. Multiplex genome engineering using CRISPR/Cas systems. Science 339, 819-823 (2013); Horvath, P. et al. Diversity, activity, and evolution of CRISPR loci in *Streptococcus thermophilus*. J Bacteriol 190, 1401-1412 (2008).

As noted above, the Cas9 can be delivered as a purified protein (e.g., a recombinantly produced purified protein, prefolded and optionally complexed with the sgRNA) or as a nucleic acid encoding the Cas9, e.g., an expression construct. Purified Cas9 proteins can be produced using methods known in the art, e.g., expressed in prokaryotic or eukaryotic cells and purified using standard methodology. See, e.g., Liang et al., Journal of Biotechnology 208:44-53 (2015); Kim et al., Genome Res. 2014 June; 24(6): 1012-1019. Efficiency of protein delivery can be enhanced, e.g., using electroporation (see, e.g., Wang et al., Journal of Genetics and Genomics 43(5):319-327 (2016)); cationic or lipophilic carriers (see, e.g., Yu et al., Biotechnol Lett. 2016; 38: 919-929; Zuris et al., Nat Biotechnol. 33(1):73-80 (2015)); or even lentiviral packaging particles (see, e.g., Choi et al., Gene Therapy 23, 627-633 (2016)).

Expression Constructs

Expression constructs encoding one or both of guide RNAs and/or Cas9 editing enzymes, and/or an inhibitory nucleic acid as described herein, can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. In some embodiments, the oligonucleotide is a gapmer (contain a central stretch (gap) of DNA monomers sufficiently long to induce RNase H cleavage, flanked by blocks of LNA modified nucleotides; see, e.g., Stanton et al., Nucleic Acid Ther. 2012. 22: 344-359; Nowotny et al., Cell, 121:1005-1016, 2005; Kurreck, European Journal of Biochemistry 270:1628-1644, 2003; FLuiter et al., Mol Biosyst. 5(8):838-43, 2009). In some embodiments, the oligonucleotide is a mixmer (includes alternating short stretches of LNA and DNA; Naguibneva et al., Biomed Pharmacother. 2006 November; 60(9):633-8; Ørom et al., Gene. 2006 May 10; 372( ):137-41). Representative United States patents that teach the preparation of such hybrid structures comprise, but are not limited to, U.S. Pat. Nos. 5,013,830; 5,149,797; 5,220,007; 5,256,775; 5,366,878;

5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3OCH_3$, $OCH_3O(CH_2)n$ $CH_3$, $O(CH_2)n$ $NH_2$ or $O(CH_2)n$ $CH_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-$CH_2CH_2OCH_3$, also known as 2'-O-(2-methoxyethyl)] (Martin et al, Helv. Chim. Acta, 1995, 78, 486). Other preferred modifications include 2'-methoxy (2'-0-$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science and Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention can include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I Theory and Nucleic Acid Preparation*, Tijssen, ed. Elsevier, N.Y. (1993).

Pharmaceutical Compositions

The methods described herein can include the administration of pharmaceutical compositions and formulations comprising inhibitors of OR14I1 or DMBT1, e.g., small molecules, inhibitory antibodies, peptides or nucleic acid sequences designed to target or inhibit OR14I1 or DMBT1; or inhibitors of adenylyl cyclase.

In some embodiments, the compositions are formulated with a pharmaceutically acceptable carrier. The pharmaceutical compositions and formulations can be administered parenterally, topically, orally or by local administration, such as by aerosol or transdermal application. In some embodiments, for treatment of infection, systemic and/or organ system-targeted delivery (e.g., to the GI tract) is used. Thus in some embodiments, administration is oral or parenteral, e.g., by injection or IV. For preventing infection (prophylaxis), oral and nasal delivery, or vaginal, rectal and/or oral delivery could be used to possibly prevent sexual transmission. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylenestearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater. Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy,* 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy,* 21st ed., 2005.

Various studies have reported successful mammalian dosing using complementary nucleic acid sequences. See, for example, Esau C., et al., (2006) Cell Metabolism, 3(2):87-98; Krützfeldt J., et al., (2005) Nature 438, 685-689; Elmen J., et al., (2008) Nature 452, 896-899.

Combination Therapies

The methods can also include administration of a standard treatment for CMV infection, e.g., using antiviral compounds, immunomodulators, immunostimulants, antibiotics, and other agents and treatment regimes (including those recognized as alternative medicine) that can be employed to treat CMV-associated conditions (e.g., retinitis, pneumonitis, restenosis, cervical carcinoma, prostate cancer, adenocarcinoma of the colon, disseminated viremia, and organ disfunction). Antiviral compounds include, but are not limited to, ddI, ddC, gancyclovir, fluorinated dideoxynucleotides, nonnucleoside analog compounds such as nevirapine (Shih, et al., PNAS 88: 9978-9882 (1991)), TIBO derivatives such as R82913 (White, et al., Antiviral Research 16: 257-266 (1991)), and BI-RJ-70 (Shih, et al., Am. J Med. 90 (Suppl. 4A): 8S-17S (1991). Immunomodulators and immunostimulants include, but are not limited to, various interleukins, CD4, cytokines, antibody preparations, blood transfusions, and cell transfusions. Antibiotics include, but are not limited to, antifungal agents, antibacterial agents, and anti-*Pneumocystis carinii* agents.

EXAMPLES

The invention is further described in the following examples, which do not limit the scope of the invention described in the claims.

Materials and Methods

The following materials and methods were used in the present examples.

Cell Culture and Infections

Cells. ARPE19 epithelial cells (American Type Culture Collection (ATCC); Manassas, VA, USA) were grown in DMEM-F12 medium (ATCC) supplemented with 10% fetal bovine serum (FBS). Human embryonic lung (HEL) fibroblasts, HEK293T cells were obtained from ATCC and grown in cultured in Dulbecco's Modified Eagle Medium (DMEM) supplemented with 10% FBS and 1% penicillin-streptomycin. HeLa-H1 cells (ATCC) were grown in minimal essential medium (MEM) supplemented with 10% fetal calf serum (FCS), 100 U/ml penicillin, 100 µg/ml streptomycin, and 2 mM L-glutamine. All media, serum, and antibiotics were from Gibco.

Sf9 insect cell lines (ATCC) were cultured in suspension in a rotary shaker at 27° C. in Sf 900 II SFM medium (ThermoFisher). Cell density and viability were assessed by Trypan blue staining. Cell viability were calculated on the basis of the percentage of living cells with respect to the total number of cells at various times post-infection. The viability of the cells at the moment of infection was >99% in suspension.

Viruses. HCMV AD169 (ATCC) was propagated in HEL fibroblasts by infecting at an MOI of 0.01 followed by culturing the cells until a cytopathic effect was observed. Virus was prepared by sonicating the cells, followed by centrifugal clarification. Titering was done using a standard plaque assay on HEL fibroblasts. HCMV TB40E-GFP virus was generated from a bacterial artificial chromosome (BAC, Eain Murphy, Cleveland Clinic). Infectious HCMV was recovered by electroporation of BAC DNA into HEL fibroblasts as described (A. M. Paredes, D. Yu. Curr Protoc Microbiol Chapter 14, Unit14E 14 (2012). TB40E-GFP was adapted to ARPE19 epithelial cells through 8 passages, infecting at an MOI of 0.1 for each passage. Viral stocks of TB40E-GFP were generated and titered as described for AD169. TR5 and TR5ΔUL128-131 were from Patrizia Caposio (J. H. Kim, D. Collins-McMillen, P. Caposio, A. D. Yurochko. Proc Natl Acad Sci USA 113, 8819-8824 (2016)) (Oregon Health and Sciences University). TB40EΔUL128-131 virus was generated by BAC recombineering using the same primers and protocol used to create TR5ΔUL128-131 (J. H. Kim, D. Collins-McMillen, P. Caposio, A. D. Yurochko. Proc Natl Acad Sci USA 113, 8819-8824 (2016)). BADwt (D. Yu, G. A. Smith, L. W. Enquist, T. Shenk. J Virol 76, 2316-2328 (2002)) is derived from a BAC clone of HMCV AD169. BADrUL131 (D. Wang, T. Shenk. Proc Natl Acad Sci USA 102, 18153-18158 (2005); D. Wang, T. Shenk. J Virol 79, 10330-10338 (2005)) is a PC-expressing derivative of BADwt in which the UL131 ORF has been repaired. Both clones were provided by Tom Shenk (Princeton University). In each experiment, HEL or ARPE19 cells were infected with HCMV at the noted MOI for 2 h at 37° C., except for viral binding studies which were done on ice. Recombinant retroviruses and lentiviruses were produced in HEK293T cells and titered by infecting H1-HeLa cells with serial dilutions of virus.

HCMV Infection. HCMV infections were performed in growth medium with 2% FBS for 2 h. The viral inoculum was removed and replaced with normal growth medium.

Cloning of Human OR14I1 cDNA.

OR14I1 is a monoexonic gene whose full-length coding sequence was amplified from ARPE19 genomic DNA. Forward primer contains a NotI site and reverse primer contain a BamH1 site. After PCR amplification, reaction products were digested with Not1 and BamH1, and cloned into the Not1 and BamH1 sites of the vector. Pseudotyped viruses were produced using pCG-VSV-g and pCG-GagPol vectors. PQCXIN-Flag-OR14I1 was constructed using the same vector and same digestion sites as above. An amino-terminal FLAG epitope was added in the forward primer.

For the PQCXIN-OR14I1-rescue, a three-step PCR amplification procedure was used to generate silent mutation fragments in the guide RNA targeted region. Original sequence: TCCTACGCAGCCGTCCACACT (SEQ ID NO:8). Silent mutation sequence: AGCTATGCTGCTGTG-CATACC (SEQ ID NO:9). The final plasmid was generated using the same vector and same digestion sites as above and sequence verified.

Generating Stable ARPE19-Cas9 or HEL-Cas9 Cells and Infecting with Lentivirus sgRNA Libraries The human codon-optimized sequence of S. pyogenes Cas9 was subcloned from plasmid lentiCas9-Blast (Addgene) into the pHAGE-Hygromycin lentiviral vector (Addgene), which was used to generate lentivirus to transduce ARPE19 cells and HEL cells. Stably transduced cells were selected in the presence of hygromycin B (200 μg/ml, Life Technologies). Cas9 expression were detected in each cell lines by immunoblot. Lentivirus sgRNA libraries were generated following published protocols using the human GeCKO v.2 sgRNA library (Addgene (1)). The GeCKO v.2 library is composed of two half-libraries (library A and library B). Each half-library contains three unique sgRNA per gene. ARPE19-cas9 and HEL-cas9 Cells were transduced with lentivirus-packaged sgRNA library A and B, each at an MOI of 0.2.

Screening CRISPR Libraries with HCMV TB40E-GFP and Ad169 Virus

For each CRISPR half-library of cells, $6.5 \times 10^7$ cells were plated onto eleven 6-well culture plates to ensure sufficient coverage of sgRNAs. Each sgRNA was represented ~240 times (that is, there are on average 240 cells transduced with the same sgRNA). This representation rate was calculated from titration plates that were set up in parallel with the library. These cells were challenged with either HCMV TB40E-GFP or Ad169 in three independent screens for about 3 months (or as soon as no GFP or surviving cells remained in the ARPE-cas9 or HEL-cas9 infected cells for the TB40E-GFP-infections). Cells were then washed three times with PBS to remove loosely attached round-shaped cells. The surviving population were re-seeded and cultured with normal medium until ~70% confluence. Cells were then subjected to a second round of infection with TB40E-GFP or AD169. The surviving population were harvested and their genomic DNA were extracted using the DNeasy Blood and Tissue DNA mini kit (Qiagen). Chromosomally integrated sgRNAs were amplified by PCR performed using Herculase II Phusion DNA polymerase (Agilent), and primers flanking the sgRNA: lentiGP-1_F (AATGGACTATCATATGCTTAC CGTAACTTGAAAGTATTTCG (SEQ ID NO:10)) and lentiGP-3_R (ATGAATACTGCCATTTGTCTCAA-GATCTAGTTACGC (SEQ ID NO:11)). The gel-purified PCR product was 5'-phosphorylated and ligated to adapters and barcodes, gel-purified and NGS was performed on an Ion Proton sequencing platform (Life Technologies). The FASTQ files were trimmed using the Cutadapt program, and then mapped to the sgRNA library key using the Bowtie2 program. Read counts for each sgRNA were calculated using the Samtools program and custom Matlab scripts. Selected candidate genes were chosen for further study if they had >20 reads per sgRNA across >3 independent sgRNAs. Each screen was performed three times.

Data Processing and Initial Analysis

Raw FASTQ files were trimmed of excess sequences using the software module cutadapt, by identifying and removing flanking sequences (5' end: GAAAGGACGAAACACC (SEQ ID NO:12), 3' end: TTTCTAGCTCTAAAAC (SEQ ID NO:13)) in each read, and subsequent mapping to the guide library using bowtie2 software on UMass Medical School's Green Hill High Performance Computing Cluster (GHPCC). Read counts for each sgRNA were calculated using samtools. Only sgRNAs with twenty or more sequencing reads were used for analysis. Identified genes were ranked according to the number of total reads and according to the number of retrieved independent sgRNAs per gene (the human GeCKO v2.0 library contains six independent sgRNAs per gene).

Figure 2A:
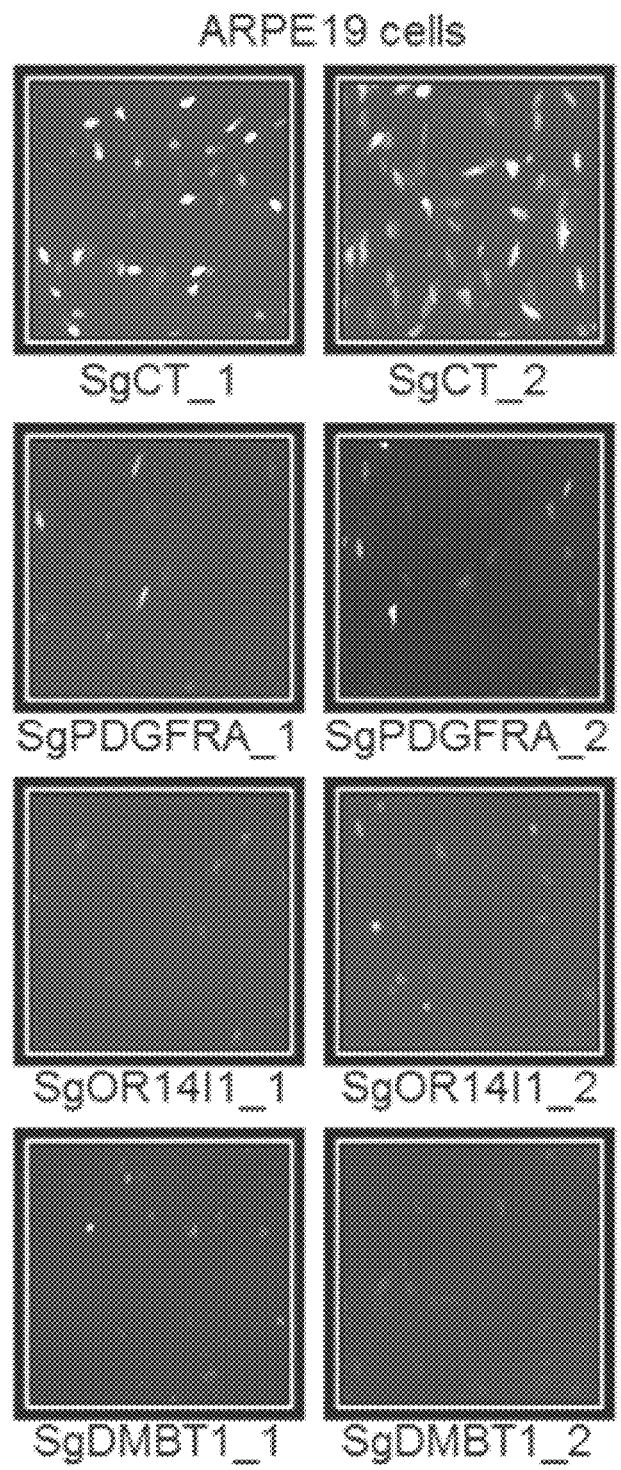
Figure 2B:
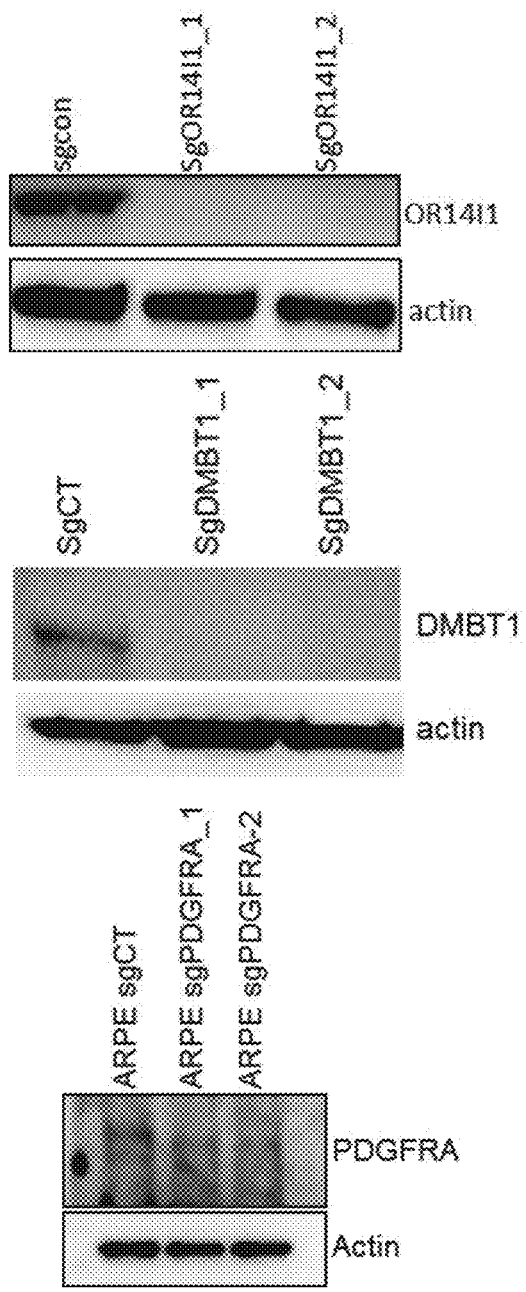
Figure 2C:
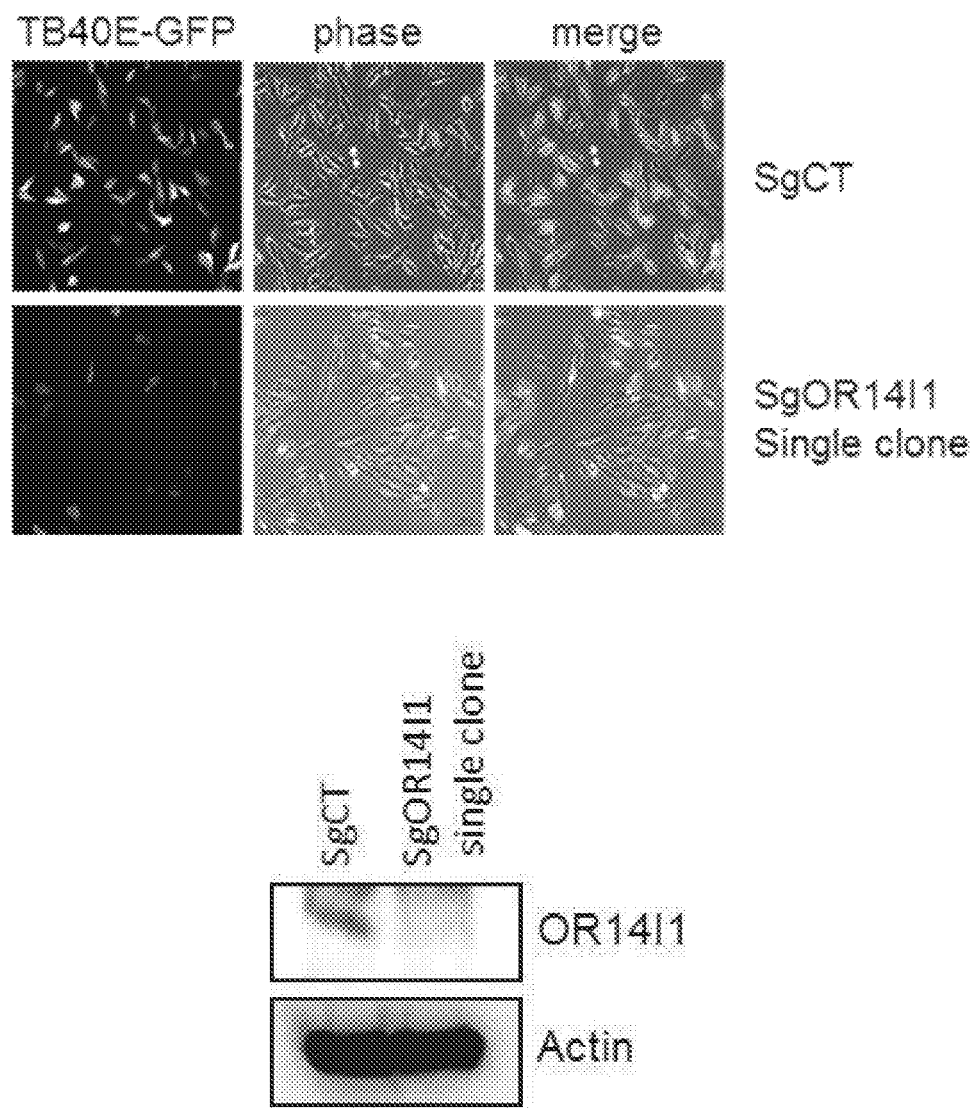

Candidate gene selection criteria were: over 20 reads per guide, 3 or more independent guides per gene, and scoring in HCMV TB40E-GFP infected ARPE19 cells, but not in HCMV Ad169 infected HEL cells (FIG. 2A). The common or specific sgRNA between two strains on two cell types were analyzed with proprietary Matlab scripts. If the reads specifically appeared in the HCMV TB40E-GFP infected ARPE cells, but not in infected HEL cells, we called these unique targets; if the reads appeared in both HCMV TB40E-GFP infected ARPE19 cells and HCMV Ad169 infected HEL cells, we called these common targets (FIG. 2A). For a manually curated list of cell surface proteins, the knockout phenotype was verified by transfer of individual sgRNAs.

ARPE Knockout Cell Lines

The following sgRNA sequences were cloned into LentiGuide-Puro vectors (Addgene, Plasmid #84752) to target the indicated genes: GACCTTCAATGGACTTACCC (PDGFRA_1; SEQ ID NO:14), AGCTATGGGGACTTCC-CATC (PDGFRA_2; SEQ ID NO:15), TCC-TACGCAGCCGTCCACAC (OR14I1_1; SEQ ID NO:16), TGAGCACCGTTGAGAAGATT (OR14I1_2; SEQ ID NO:17), TTACCGTAGTCTGTAGTCCT (DMBT1_1; SEQ ID NO:18), CGCAGCTTCACTGATTCCCT (DMBT1_2; SEQ ID NO:19), CGGGATGCAGCTGGAGAGGA (CON_1; SEQ ID NO:20), CCAGTTGCTCTGGGG-GAACA (CON_2; SEQ ID NO:21). ARPE19-Cas9 or HEL-cas9 cells were transduced with lentiviruses to express each sgRNA. Populations of stable cells were selected with puromycin (2.5 µg/ml) and hygromycin B (200 µg/ml).

ARPE19-Cas9 or HEL-Cas9 fibroblasts were transduced with lentiviruses and selected with puromycin (2.5 µg/ml). Clonal OR14I1−/− cells were generated by serial dilution. Small clones were detected by microscopy after 1 week and followed for ~3 weeks. Isolated colonies, which represent individual, clonally derived knock out cells, were isolated and expanded. DNA was isolated from cells representing clones and both alleles were confirmed as successfully targeted by sequencing.

ARPE Knock Down Cell Lines

Each shRNA was cloned into the pLKO.1-blast (Addgene) lentiviral vector followed by viral packing and multiple rounds of amplification in 293T cells. Essentially, the pLKO.1-blast constructs and packaging plasmids were co-transfected into 293T cells with the resulting supernatant harvested at 36 h. Lentiviruses were recovered by ultracentrifugation for 2 h at 28,000 rpm in a Beckman SW28 rotor and resuspensed in DMEM. The lentiviruses were used to transduce the ARPE19 or HEL cells to generate shRNA knock down cells. Populations of stable cells were selected with blasticidin (Invitrogen, 10 µg/ml) for 1 week.

shRNA Sequences:

```
                            (SEQ ID NO: 22)
shOR14I1:    GCAGAAGCTCCATCTCTTATC (SEQ ID NO: 23)
shDMBT1:     GGAGTCAACTGTAGCAGAAGG (SEQ ID NO: 24)
shPDGFRA:    GCCTTTGTACCTCTAGGAATG (SEQ ID NO: 25)
shCON:       AATTTTTTCCCCAAAGGGGG
```

Immunoblot Analysis

Mock and infected cells were harvested at the indicated times pi and cells pellets were stored at −80° C. Thawed cell pellets were resuspended in radioimmunoprecipitation assay buffer (RIPA (2)), and incubated on ice for 1 h. Samples were sonicated for 15 s, and soluble proteins were collected by centrifugation for 10 min at 13,000 rpm in a microcentrifuge. Proteins were resolved by SDS-PAGE, and transferred to polyvinylidene difluoride membranes (Perkin-Elmer) by electroblotting. Detection of proteins was performed with antibodies specific for HCMV pp65 (Virusys Corporation, CA003-100), OR14I1 (Aviva Systems Biology, ARP71293-P050); PDGFRα (EMD Millipore, 07-276); DMBT1(G-4) (Aanta Cruz Biotechnology, sc-514566); AKT(Pan)(C67E7) (Cell Signaling, 4691); phospho-AKT(ser473) (Cell Signaling, 9271); and Actin (Sigma, A5316). Horseradish peroxidase (HRP)-conjugated secondary antibodies (GE Healthcare Life Sciences) were used for binding to the primary antibody. Protein bands were visualized in G:Box (Syngene) by chemiluminescence using ECL reagent (Perkin-Elmer).

Imaging

Live cell images: Phase and GFP signal images were captured on a Zeiss microscope (Zeiss AxioObserver Z1) at 10× magnification. Fixed cell images: cells were washed with PBS (Life Technologies) and fixed with 4% formalin in PBS (Sigma). DNA was stained with Hoechst 33342 dye (Life Technologies). The fixed cells were imaged using an Image Xpress Micro (IXM, Molecular Devices) at 4× magnification. Images were analyzed with MetaXpress imaging software (Molecular Devices) to determine the total cells per well and the percentage of infected cells (GFP positive) in each well. For IE immunostaining: fixed cells were permeabilized with 0.2% Triton X-100 (Sigma) in PBS. Blocking was performed with 1% BSA (Calbiochem, 2930) in PBS with 0.3M glycine (Sigma). Cells were then incubated in antibody targeting the major IE proteins (IE, EMD Millipore, MAB8131) diluted in 1% BSA in PBS. Cells were then incubated in secondary antibody (Texas Red-conjugated goat anti-mouse IgG2A, Southern Biotech, 1080-07) in PBS containing 1% BSA.

Flow Cytometry 48 h after HCMV TB40E-GFP infection, ARPE19 cells were then treated with cell dissociation buffer (Gibco) and incubated at 37° C. for 10 min. Samples were then washed three times with cold buffer and fixed with cold 2% paraformadehyde in PBS. Cells were pelleted and washed and resuspended in washing buffer (0.1% tween-20 in PBS). Finally, the cells were resuspended in staining buffer (1% BSA, 0.1% sodium azide in HBSS) after pelleting again and immunofluorescent cells analyzed using a MACSQUANT analyzer 10 (Miltenyi Biotec) using blue laser 488 nm and filter 525/50 nm. Results were analyzed using FLOWJO V9.9 image analysis software.

Cell-Binding Virus Assay

The shPDGFRA, shOR14I1 and shDMBT1 transduced ARPE19 cells were chilled on ice for 20 min and then incubated with chilled TB40E-GFP at the indicated MOT on ice for 1 h. The cells were then washed ten times with cold PBS. Cellular DNA and cell-associated viral DNA were isolated using a DNeasy Blood & Tissue Kit (Qiagen). Viral DNA (UL83) and host DNA ((β-ACTIN) was quantified by real-time quantitative PCR as described (E et al., J Virol 88, 2279-2290 (2014)).

Cell-Internalized Virus Assay

In parallel to the virus binding assay, a subset of plates were then shifted to 37° C. for 2 h to allow virus entry. Virions that did not penetrate the cells were removed by EDTA-trypsin treatment. After 10 cold PBS washes, internalized viral DNA levels were quantified by qPCR.

Generating ARPE OR14I1 Rescue Cell Lines

Retrovirus production and transduction. The OR14I1 cDNA with silent mutations on the guide RNA regions was subcloned into the BamHI and AgeI sites of the pQCXIN gammaretroviral vector (Clontech). For retrovirus production and transduction, HEK293T cells were transfected with Mirus 293T lipid (Mirus) together with the retroviral plasmids pQCXIN-OR14I1(5 µg), pCG-GagPol (2 µg), and pCG-VSV-g (2 µg). After 48 h, the retrovirus-containing supernatant was filtered (0.45-um-pore-diameter low-protein-binding filter; Millipore), supplemented with 8 µg/ml Polybrene (Sigma), and then added to APRE cells that were deleted for OR14I1, which had been plated at 3×10$^5$ cells per 6-cm-diameter dish. This transduction was repeated with second round of infection with 72 h retroviral supernatant. Forty-eight hours after the second transduction, cells were replated, incubated overnight, and then selected with 200 µg/ml of Geneticin (Invitrogen) for 1 week. Rescue was confirmed by immunoblotting for OR14I1 expression.

Real-time Quantitative PCR Analysis of Viral DNA Synthesis

DNA was isolated from infected ARPE cells using the Dneasy Blood and Tissue DNA mini kit (Qiagen) according to the manufacturer's instructions. Viral genomes were quantified with a primer pair (pp549s and pp812as) and a probe (pp770s) for UL83 (3), and the number of viral genomes normalized to the number of cellular copies of β-ACTIN with a previously described set of primers and probe (4). Unknown sample values were determined on the basis of a standard curve of known copy numbers of UL83 (AD169-BAC) and β-ACTIN (pAB1-bactin-PCRscript) (kind gifts from Donald Coen, Harvard Medical School). PCR mixtures contained 1 µl of 100 µl extracted DNA, 900 nM primers, 250 nM probe, 10 µl TaqMan Universal PCR master mix (Roche), and nuclease-free water (Ambion) to 20 µl. Real-time PCR was performed and analyzed by using a ViiA7 Real-Time PCR System (Applied Biosystems).

Expression of OR14I1 in Sf9 Cells

OR14I1 cDNA was flagged at the N-terminus and subcloned into BamHI and XhoI sites of the pFasBac/CT-Topo vector (ThermoFisher). The pFasBac-OR14I1 construct was then transformed into DH10Bac *E. coli* for transposition into a bacmid. The recombinant bacmids were transfected into Sf9 cells using Cellfectin® II Reagent (Invitrogen) to produce recombinant baclovirus (rBacs) following the manufacturer's instructions. The resulting rBacs were then passaged twice and titrated in duplicate by plaque assay. Sf9 cells were infected with the rBacs at a MOI of 0.1. The flag-OR14I1 protein expression in Sf9 cells was checked by immunoblot.

Membrane Vesicle Preparation

One liter cultures of Sf9 cells were harvested at 4 dpi with the recombinant OR14I1 baculovirus. Pellets were washed twice with PBS-buffered saline (PBS), resuspended in 60 ml of hypotonic lysis buffer (20 mM Tris, pH 8.0, 25 mM NaCl, 2 mM $MgCl_2 \cdot 6H_2O$; 1 mM $EDTA \cdot Na_2(H_2O)_2$, 2 mM TCEP-HCl, complete EDTA-free tablets, 1 table/50 ml) and cells were allowed to swell on ice for 15 min. The cell suspension was subjected to 100 strokes with a type B (Tight) Dounce homogenizer. Unlysed cells and cell debris were removed by low speed centrifugation (1,000 rpm). The membrane-containing supernatant was subjected to ultracentrifugation in SW 28 rotor at 28,000 rpm for 1 h to yield a crude membrane pellet that was resuspended in wash buffer (20 mM Tris, pH 8.0, 25 mM NaCl, 1 mM $MgCl_2 \cdot 6H_2O$, 2 mM TCEP-HCl, complete EDTA-free tablets, 1 tablet/50 ml). After a second ultracentrifugation, the membrane pellet was resuspended in freezing medium (wash buffer with 2 mM $MgCl_2$, and 10% glycerol) and stored at −20° C.

Membrane Flotation Assay

A total of 6 ul of purified HCMV TB40E-GFP virus, containing $1 \times 10^5$ pfu, was mixed with 20 ul of either Sf9-control, or Sf9-Or14I1 membrane particles and incubated at 37° C. for 30 min at 700 rpm in an Eppendorf thermomixer. A 26 ul aliquot of the membrane particles/virus mix was then mixed with 59 ul of a 70% sucrose in PBS. This mixture was placed at the bottom of a Beckman centrifuge tube (7 mm×20 mm), and 100 ul of a 41% sucrose in PBS was added on top of the sample, followed by 25 ul of a 20% sucrose in PBS. The sample was then centrifuged for 1 h at 390,000×g at 4° C. using a Beckman Optima™ TLX ultracentrifuge with a Beckman TLA-100 rotor. Twenty-three microliter fractions were collected from top to bottom and analyzed by immunoblotting.

Image Xpress Micro (IXM) Scanning

At 2 dpi with HCMV TB40E-GFP virus at the indicated MOI, ARPE19 cells were fixed with 4% formaldehyde and nuclei stained with Hoechst 33342. ARPE19 cells were imaged on an automated IXM scanning microscope. Numbers of infected cells were determined by calculating the percent GFP positive cells using MetaXpress software.

Neutralizing Assay

HCMV UL130 (40 ug/ml) or UL128 (20 ug/ml) targeted neutralizing antibodies ((5) graciously provided by Tom Shenk, Princeton University) were preincubated with HCMV TB40E-GFP virus for 2 h at room temperature. The mixtures were then incorporated into the membrane floating assay.

In Vitro Blocking Assay.

TB40E-GFP virus was incubated with Sf9-control or Sf9-Flag-OR14I1 containing membrane vehicles (40 µg/ml) for 2 h at 37° C. in a thermomixer. ARPE19 cells were chilled and then incubated with resultant chilled virus on ice for 1 h (MOI=3.0).

3D Structure Prediction and Peptide Synthesis

OR14I1 structure was predicted using SWISS-MODEL with 4 mbs.1.A (7-transmembrane CCR5 Chemokine Receptor) as a template and visualized using Swiss-PdbViewer 4.1.0. Regions of OPR14I1 predicted to be on the cell surface were identified and synthesized (peptide sequences are listed in FIG. 6B). Peptide syntheses were performed by GenScript and Bachem.

Peptide Blocking Assay

The noted synthetic peptides (100 ug/ml each or as described) were mixed with TB40E-GFP virus ($1.2 \times 10^6$ PFU) and incubated at 37° C. for 2 h by rocking. The resulting samples were then subjected to the virus binding or infection assay.

cAMP/PKA Signaling Pathway Modulation.

H-89, SQ22536 and Foskolin were purchased from Sigma-Aldrich Chemicals. Wild type ARPE19 or ARPE19 cells expressing the indicated shRNAs were treated with protein kinase A (PKA) inhibitor H-89 (20 µM), adenylate cyclase antagonist, SQ22536 (150 µM), or adenylate cyclase activator, forskolin (FSK; 20 µM) for 2 h prior to infection with TB40E-GFP (MOI=2.0). After 2 h, the medium was then replaced by the standard medium that also contained the noted small molecules. Images were taken at 2 dpi.

Determining PI3/Akt Signaling Induced by the Virus Binding.

Cells were serum starved at 37° C. for overnight and cells were pretreated with DMSO (DMSO-carrier control) or LY294002 (50 uM) in serum-free medium prior to infection for two hours. Cell plates were cooled on ice for 30 mins. Cells were infected by purified TB40E-GFP virus (no serum) at MOI of 2.0 PFU per cell for 2 hours on ice. Cell plates were shifted to 37° C. incubator (time 0). Cell were harvested at 0, 5, 10 mins post infection. Protein extracts were subjected to immunoblotting with anti-phospho Akt (ser473), Akt or anti-β-actin (loading control).

Statistical Analysis.

Statistical analyses were performed using unpaired t-tests. Values were expressed as mean±SD of three independent experiments. A p value of <0.05 was considered statistically significant. *p<0.05; p<0.01; *p<0.001; ****p<0.0001.

Example 1. CRISPR/Cas9 Screen for HCMV Host Factors

A genome-wide CRISPR/Cas9 mediated screen was performed to identify host factors that are resistant to human cytomegalovirus (HCMV) replication in epithelial cells and fibroblasts. A schematic workflow diagram of the screening process is shown in FIG. 1.

A number of host factors and pathways were shown to be enriched in the CRISPR/Cas9 mediated screens. Table 2 shows pathway enrichment of proteins identified in the ARPE19/CRISPR/Cas9 screen that are resistant to HCMV replication using ConsensusPath DB.

TABLE 2

| Enriched pathway | Number of Proteins (% of Pathway) | P-Value | Pathway Source |
| --- | --- | --- | --- |
| Signaling pathway from g-protein families | 17 (65.4) | 1.12E−05 | BiooCarta |
| Olfatory transduction - Homo sapiens (Human) | 130 (32.3%) | 1.67E−03 | KEGG |
| Neuronal System | 92 (33.9%) | 3.31E−03 | Reactome |
| G Protein Signaling Pathways | 35 (39.8%) | 9.72E−03 | Wikipathways |
| PKA-mediated phosphorylation of CREB | 9 (52.9%) | 0.0104 | Reactome |
| CREB phosphorylation through the activation of Adenylate Cyclase | 5 (71.4) | 0.0115 | Reactome |
| DNA Damage Reversal | 3 (100.0%) | 0.0145 | Reactome |
| PKA activation | 9 (56.2%) | 6.25E−02 | Reactome |
| Calcium signaling pathway - Homo sapiens (human) | 56 (33.5%) | 4.62E−02 | KEGG |

Two proteins identified in the screen were selected for further evaluation, OR14I1 and DMBT1. The sgRNA knock out ARPE-cas9 cell pools were infected with TB40E-GFP virus at MOI=3, and images of GFP expressing cells were taken 48 hours post infection (hpi). The results, shown in FIG. 2A, demonstrate resistance to HCMV TB40E-GFP strain infection in OR14I1-, DMBT1- and PDGFRA-deficient epithelial cells. Western blots, shown in FIG. 2B, confirm the deficiency of OR14I1 and DMBT1 in the cells shown in FIG. 2A. Resistance to TB40E-GFP infection was confirmed in single clone derived, diploid knockout of OR14I1 cells. The cells were infected with TB40E-GFP virus at MOI=3, and images of GFP-expressing cells were taken 48 hpi. The results demonstrated resistance to infection, see FIG. 2C.

Figure 2D:
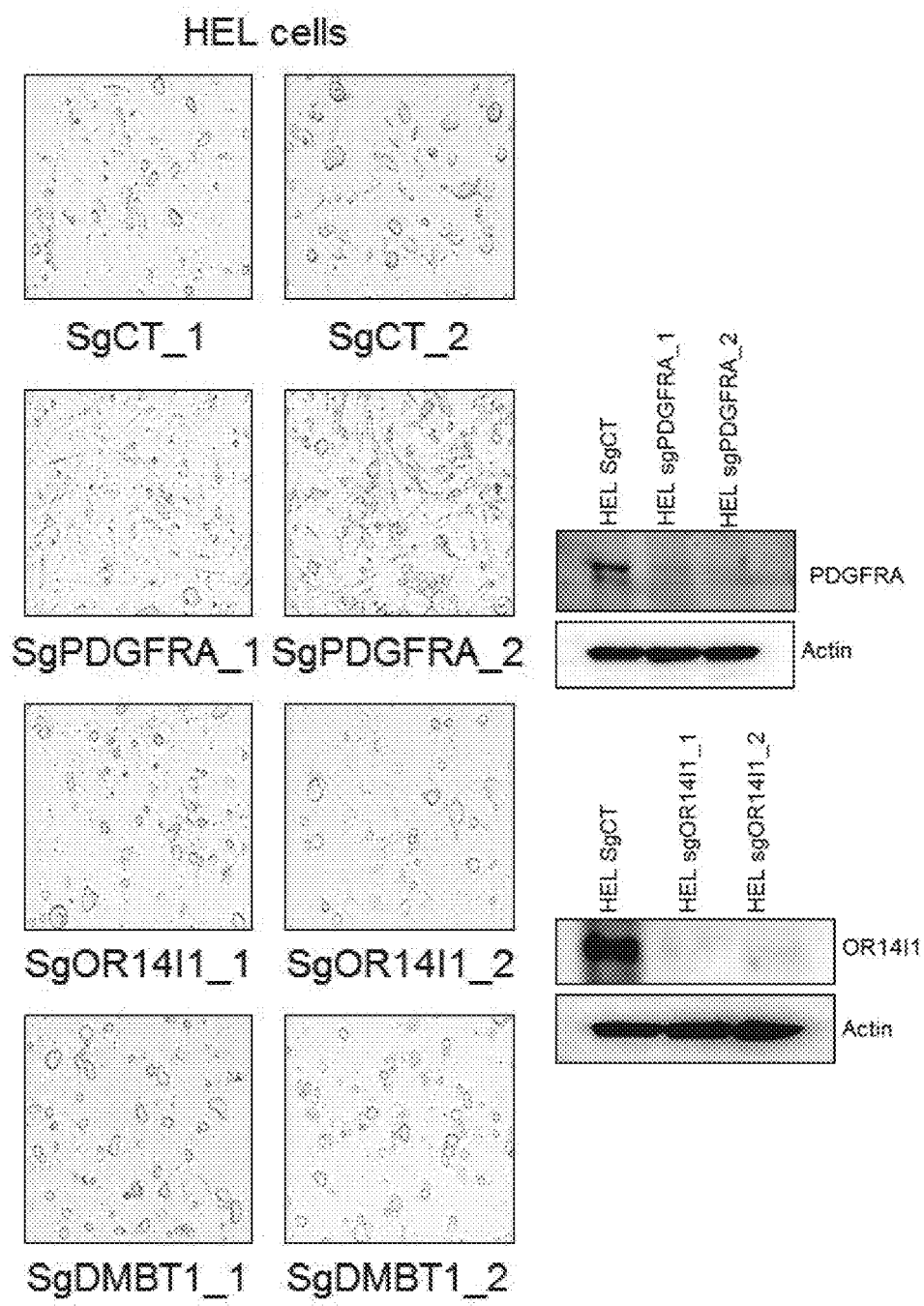
Figure 2E:
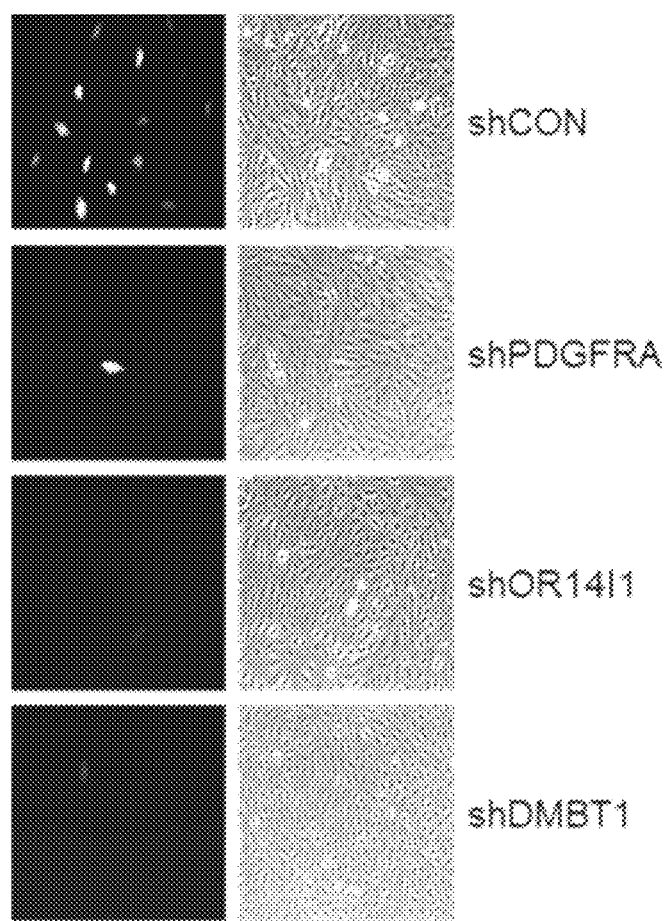
Figure 2F:
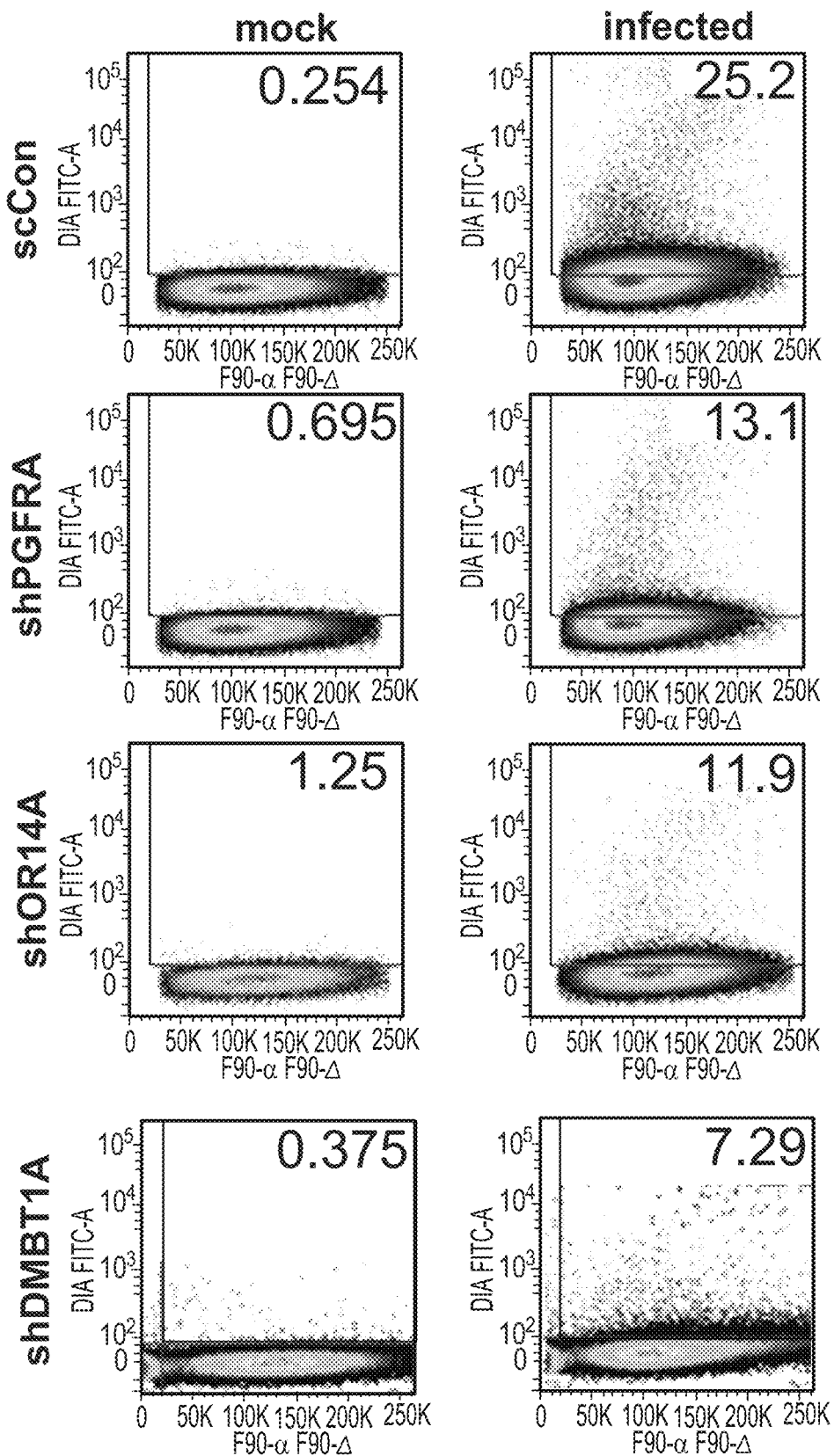
Figure 2G:
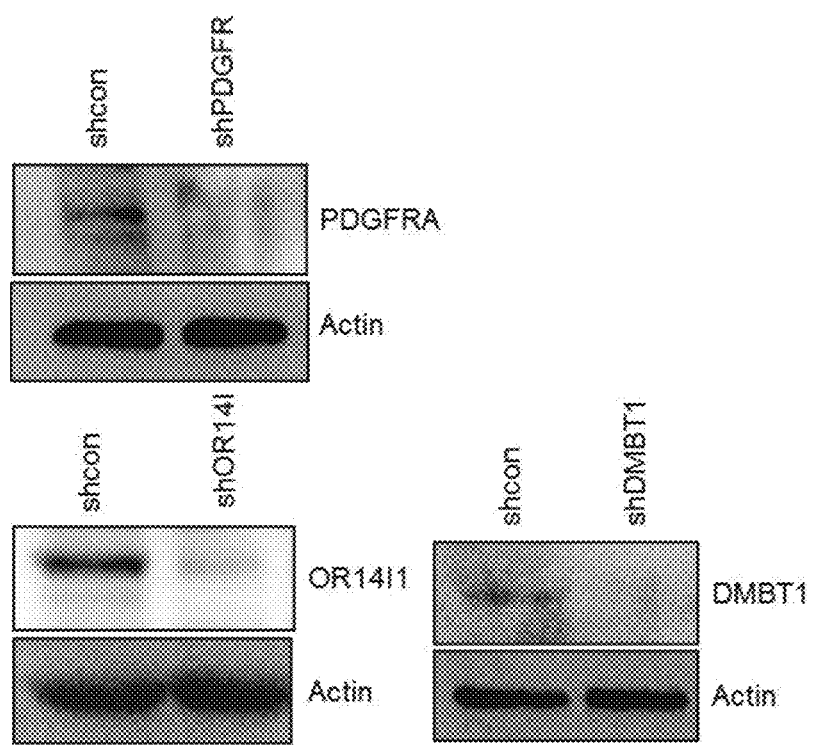
Figure 2H:
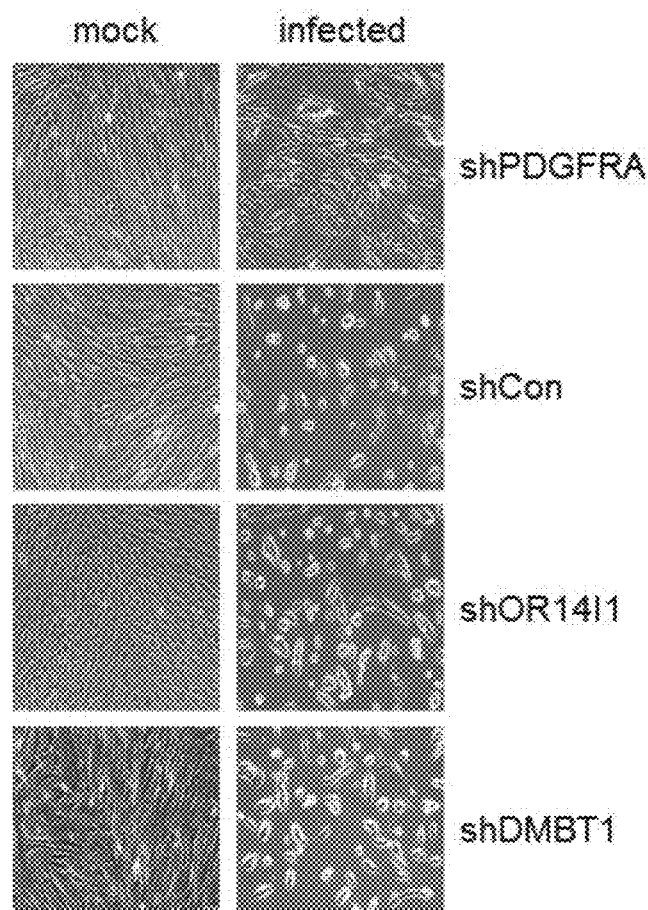
Figure 2I:
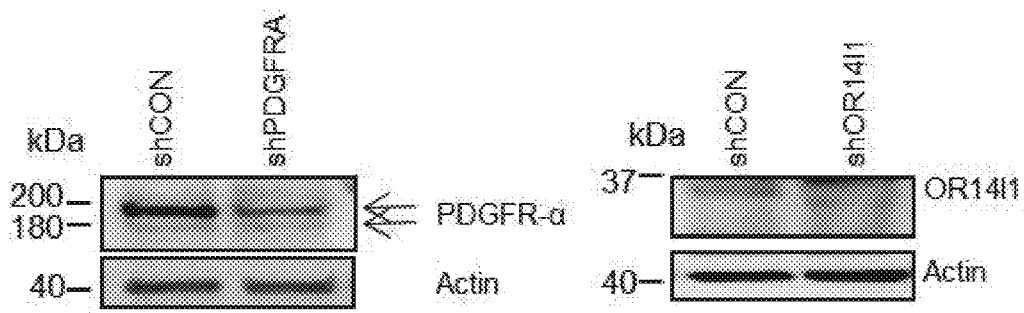

The role of these proteins in fibroblast cell-type specific tropism in HCMV infection was also evaluated. The sgRNA knock out HEL-cas9 fibroblast pools were infected with HCMV Ad169 virus at MOI=3, and images were taken 48 hpi. AD169 does not express GFP. As shown in FIG. 2D, resistance was present in PDGFRA deficient HEL fibroblasts, but not in OR14I1 or DMBT1 deficient HEL fibroblasts. HCMV infection resistance was also evaluated after knockdown using shRNA, in epithelial cells. The shOR14I1, shDMBT1 or shPDGFRA shRNA knock down ARPE19 cells were infected with TB40E-GFP virus at MOI=0.1, and images were taken 48 hpi. As shown in FIG. 2E, resistance was seen in shOR14I1, shDMBT1 or shPDGFRA knock down cells. Flow cytometry was used to analyze the percentage of GFP positive cells after infection with TB40E-GFP at 48 hpi in the shOR14I1, shDMBT1 or shPDGFRA shRNA knock down ARPE19; the results, shown in FIG. 2F, show a significant decrease in GFP-expressing cells. Western blotting was used to confirm the knockdown efficiency in the cells used in the experiments shown in FIGS. 2E and 2F. Actin is included as a loading control. Resistance to CMV infection was also evaluated in shPDGFRA, shOR14I1 or shDMBT1 knockdown HEL fibroblasts. Fibroblasts were infected with Ad169 at M01=1.0, and images were taken 48 hpi. As shown in FIG. 2H, shPDGFRA, but not shOR14I1 or shDMBT1, cells were resistant to infection. Western blotting was used to confirm the depletion of PDGFRA and OR14I1 in the cells used in the experiments shown in FIG. 2H; the results are shown in FIG. 2I.

Figure 3A:
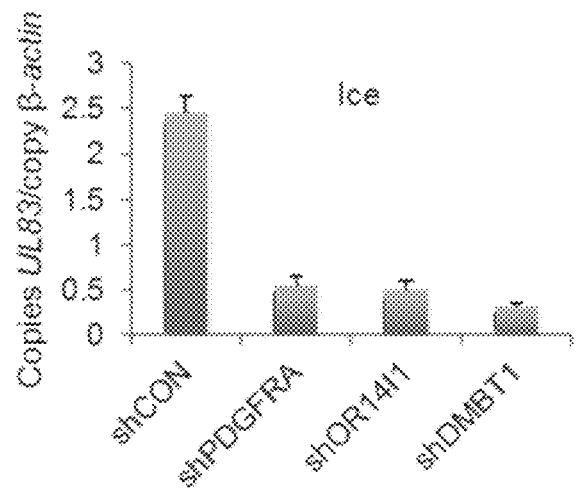
Figure 3B:
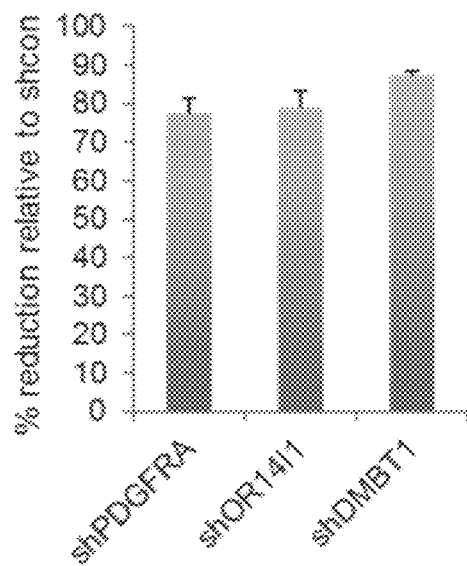
Figure 3C:
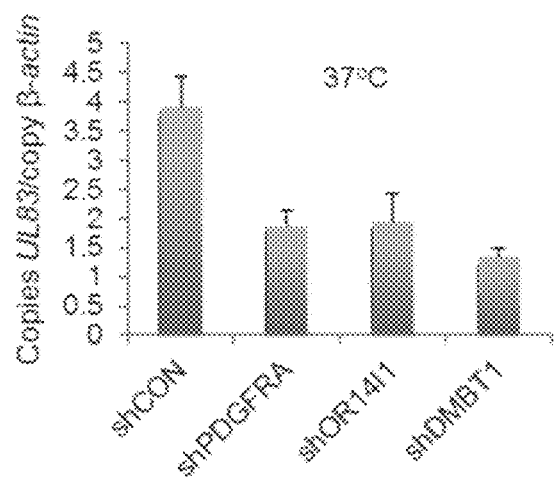
Figure 3D:
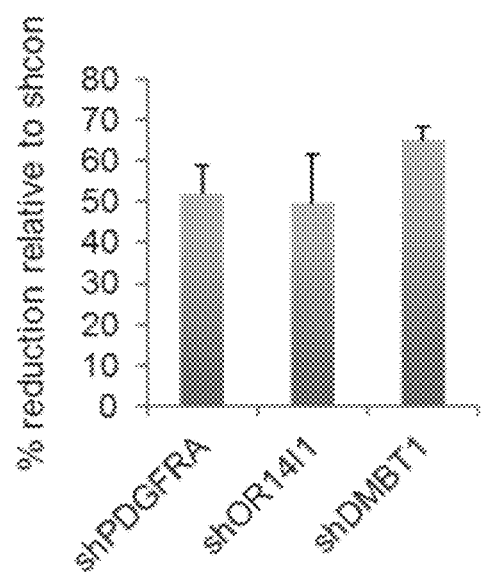

To determine whether human OR14I1 and DMBT1 are required for optimal binding of HCMV TB40E-GFP to cells, shPDGFRA, shOR14I1 and shDMBT1 transduced ARPE19 cells were infected with TB40E-GFP at an MOI of 2.0 on ice for 1 h. The cells were washed ten times with cold PBS, and viral DNA associated with the cells was quantified by qPCR. As shown in FIGS. 3A-B, OR14I1 and DMBT1 are required for optimal binding of HCMV TB40E-GFP to cells. In addition, shPDGFRA, shDMBT1 and shOR14I1 transduced ARPE19 cells were infected with TB40E-GFP at an MOI of 2.0 on ice for 1 h. The cells were then shifted to 37° C. for 2 h to allow the virus entry. Virions that did not penetrate the cells were removed by EDTA-trypsin treatment. After 10 cold PBS washes, internalized viral DNA levels were quantified by qPCR. As shown in FIGS. 3C-D, shPDGFRA, shDMBT1 and shOR14I1 transduced ARPE19 cells were resistant to infection with TB40E-GFP, with only about 50% of the viral load reduction as compared to control-infected cells, which did not make any difference to the binding step. These data demonstrated that OR14I1 play a role in binding to HCMV viron.

Figure 3E:
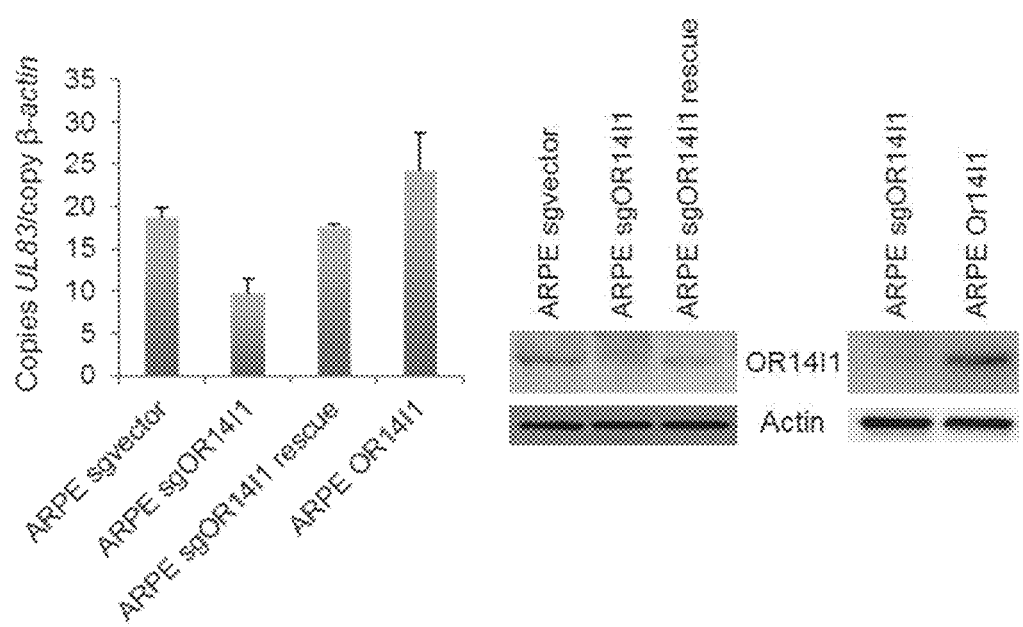

The specificity of the effect of knocking down OR14I1 was demonstrated in ARPE19-sgOR14I1 cells, ARPE19-sgOR14I1 cells rescued by transduction of a cDNA expressing OR14I1, and ARPE19-OR14I1 overexpressing cells. The cells were infected with TB40E-GFP at an MOI of 10.0 at 4° C. for 1 h. After 10 washes with cold PBS, viral DNA levels were quantified by qPCR. The results, shown in FIG. 3E, showed that expression of OR14I1 was able to rescue sensitivity to viral infection.

Figure 3F:
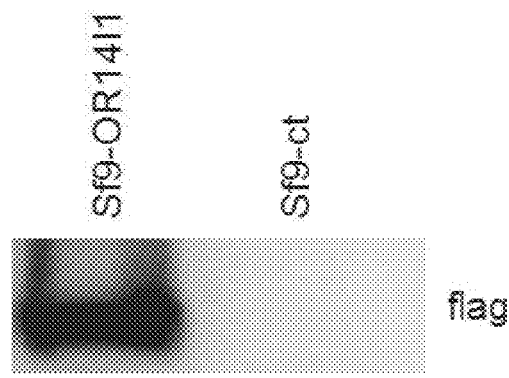
Figure 3G:
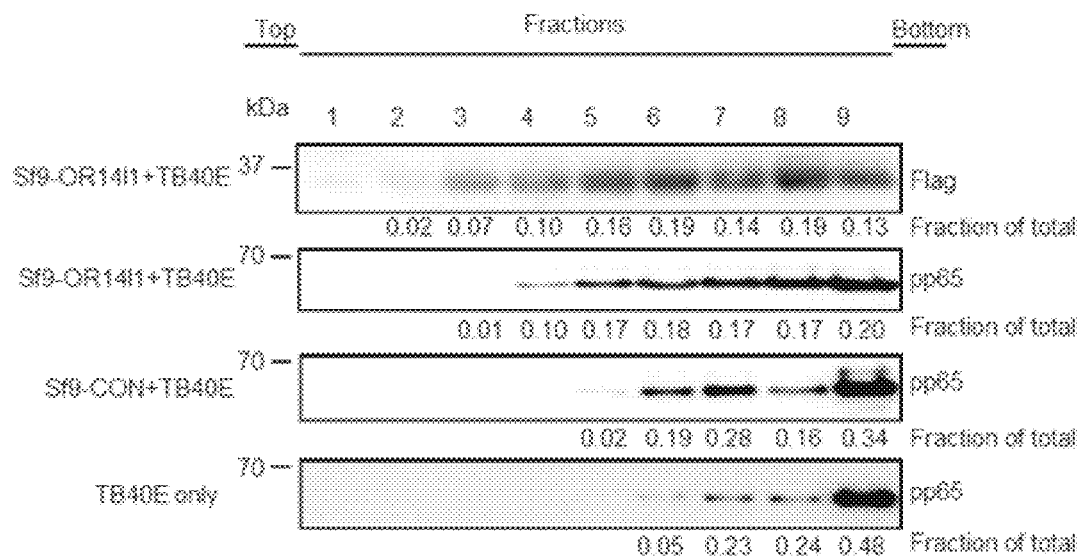

Sf9 insect cell lines expressing human OR14I1 were created to determine whether OR14I1 was sufficient for HCMV to bind cells. FIG. 3F is a Western blot showing the expression of flag-tagged human OR14I1 in Sf9 cells as detected by flag antibody. A membrane floating assay was performed on TB40E-GFP and sf9-OR14I1 membrane particles mixed and incubated at 37° C. for 1 h in an Eppendorf thermomixer. The solution was then subjected to 20 to 70% sucrose gradient centrifugation. The collected fractions were subjected to SDS-PAGE, followed by Western blotting with pp65 antibody to identify fractions containing virions. Sf9- and TB40E-GFP-only samples were used as controls. The results, shown in FIG. 3G, showed that OR14I1 can function as a receptor for TB40E-GFP binding to ARPE19 epithelial cells.

Figure 4A:
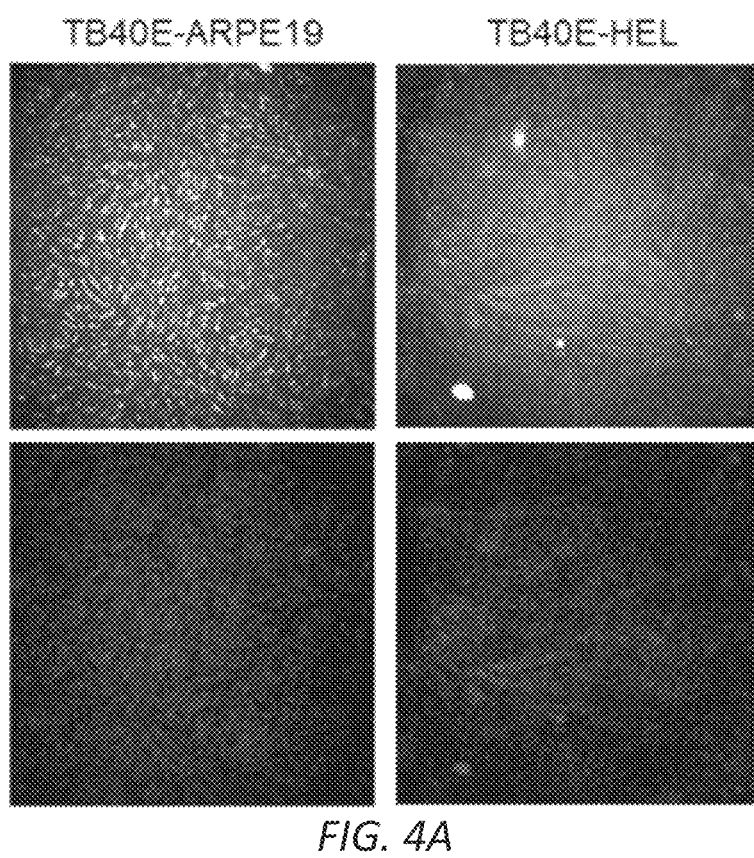
Figure 4B:
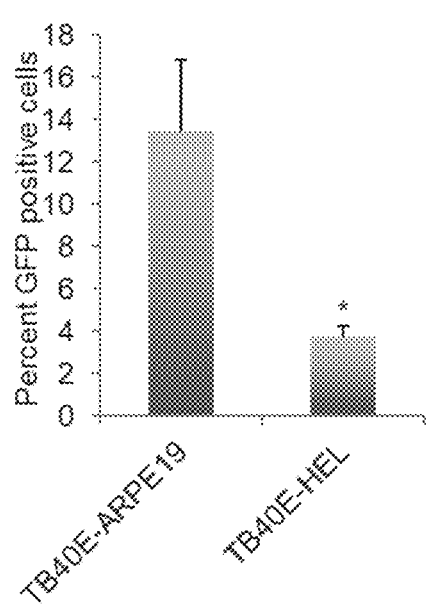
Figure 4C:
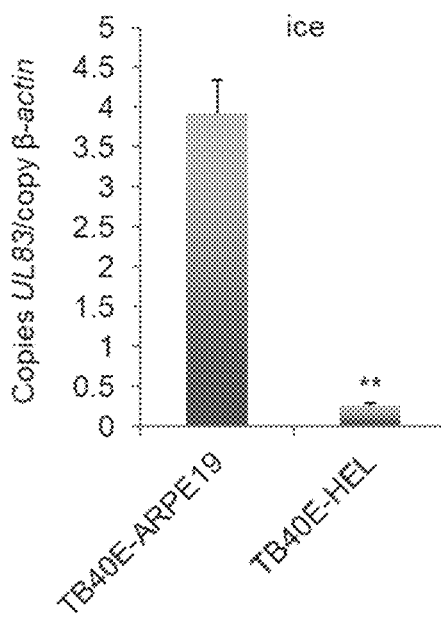
Figure 4D:
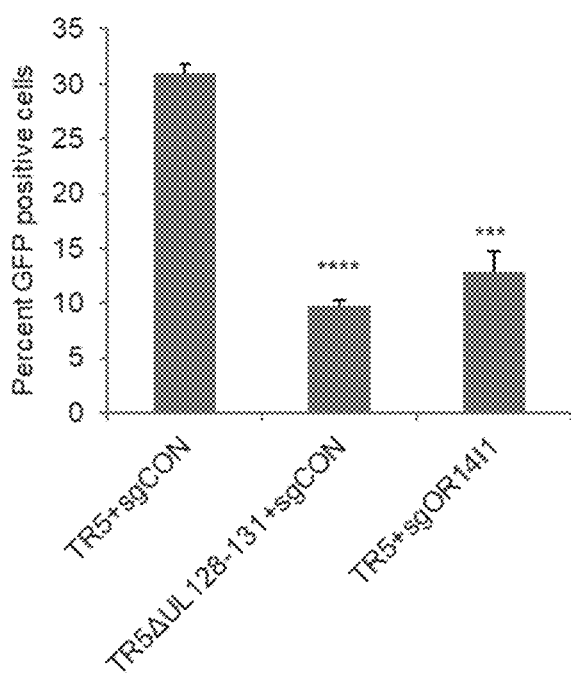
Figure 4E:
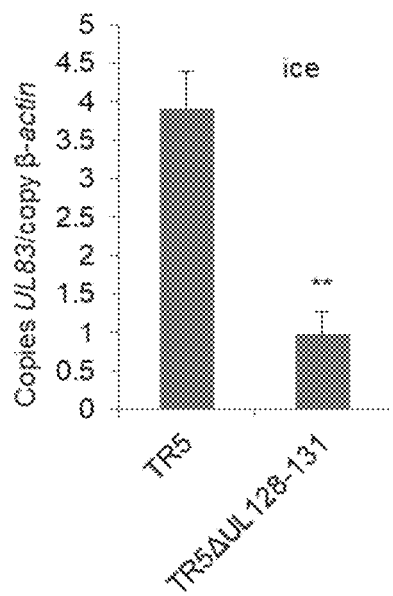
Figures 4F, 4G:
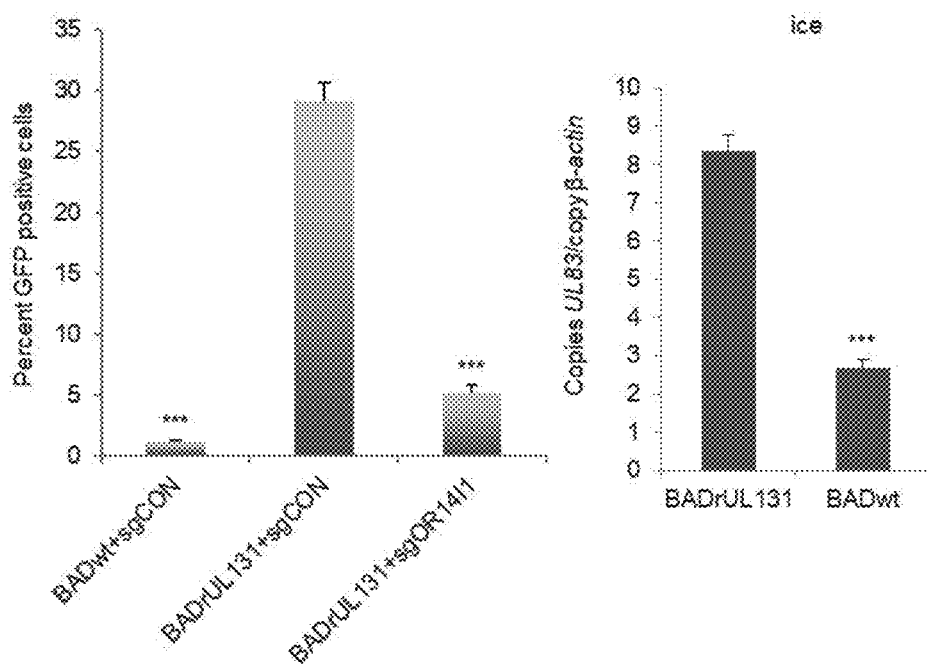

To determine whether OR14I1 binding to HCMV TB40E-GFP is dependent on virion pentameric complex (PC) proteins, ARPE19 cells were infected by TB40E-ARPE19 or TB40E-HEL at MOI=2. At 48 hpi, cells were fixed, the nuclei of the cells were stained for DNA using Hoechst 33342 dye and images taken. As shown in FIGS. 4A-B, ARPE19 epithelial cell passaged TB40E (TB40E-ARPE19) virus expressed more pentamer complex and infected epithelial cells more effectively than HEL fibroblast passaged TB40E (TB40E-HEL) virus, which had reduced virion-associated pentamer complex. In addition, ARPE19 cells were infected by TB40E-ARPE19 and TB40E-HEL virus (MOI=2) at 4° C. for 1 h. After 10 washed with cold PBS, viral DNA levels were quantified by qPCR. The results, in FIG. 4C, showed that TB40E-ARPE19 virus had improved binding ability relative to TB40E-HEL virus. Finally, UL130 or Ul128 neutralizing antibodies were preincubated with TB40E-GFP virus for 1 h at room temperature. Sf9-OR14I1 membrane particles were then added, incubated, and subjected to the floating assay; the results showed that viral binding to human OR14I1 was blocked by HCMV neutralizing antibodies that target the viral pentamer complex.

Figure 3H:
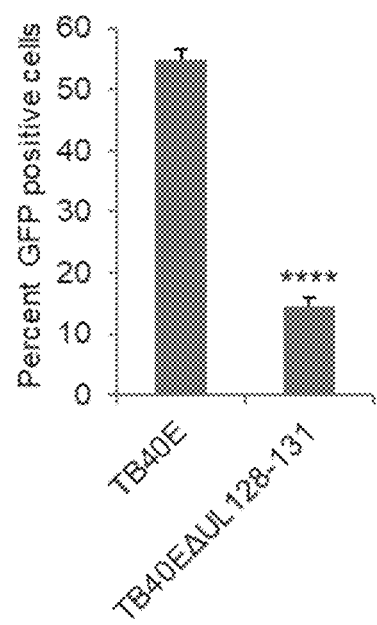
Figure 3I:
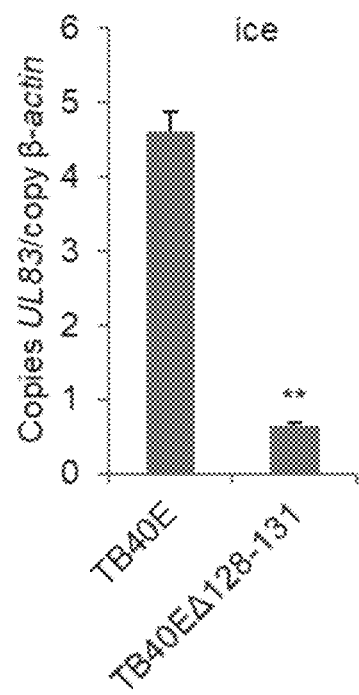
Figure 3J:
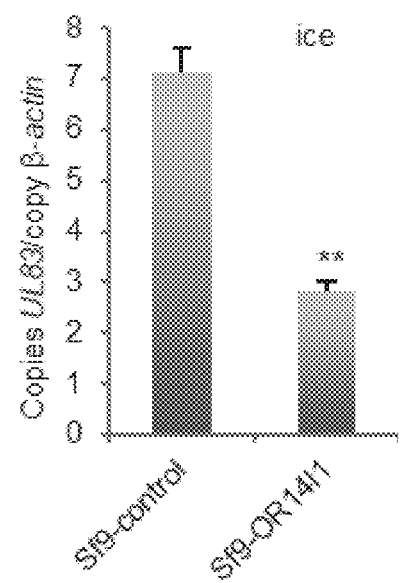

We evaluated whether TB40E binding to OR14I1 is dependent on the PC. ARPE19 epithelial cells were infected with either wildtype TB40E or TB40E lacking the PC (TB40EΔUL128-131). Consistent with published results, loss of the viral PC dramatically decreased epithelial cell infection and this correlated with a comparable loss of virus binding to the cell surface (FIGS. 3H-I). Similarly, a fibroblast-passaged virus, TB40-HEL, which has reduced levels of PC23, was deficient for both epithelial cell binding and infection (FIGS. 4A-C). A requirement for the PC to efficiently infect epithelial cells was found to be independent of the HCMV strain used (FIGS. 4D-G).

Figure 4H:
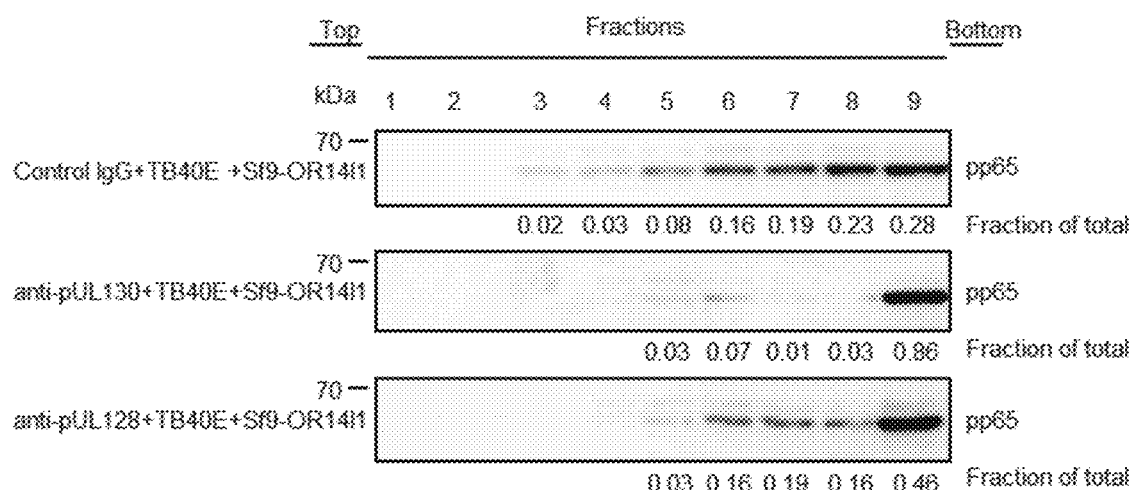

To determine if the PC is needed for HCMV binding to OR14I1, PC+ TB40E virus was pre-incubated with neutralizing antibodies6 against either of two PC subunits (pUL130 or pUl128), or a negative control antibody; Sf9-OR14I1 membrane vesicles were then added and a membrane flotation assay was performed (FIG. 4H). These assays showed that viral binding to OR14I1 was diminished by the presence of either anti-PC antibody. Furthermore, preincubation of TB40E virions with Sf9-OR14I1 membrane vesicles reduced viral binding to ARPE19 cells, demonstrating that exogenous OR14I1 competes with HCMV binding to epithelial cells (FIG. 5B). Together, these results show that the viral PC is required for interaction of HCMV with OR14I1.

Figure 5A:
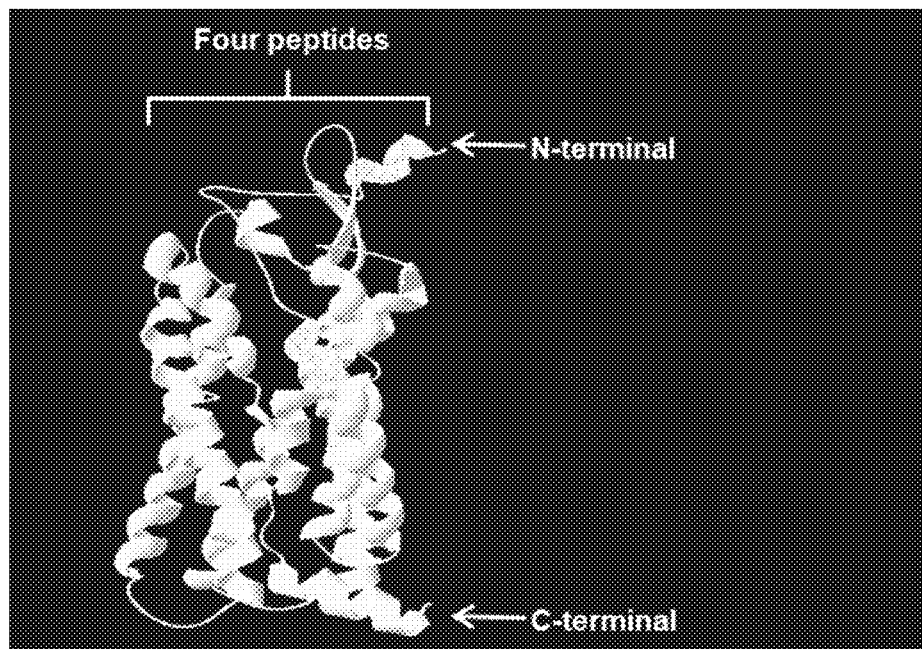
Figure 5B:
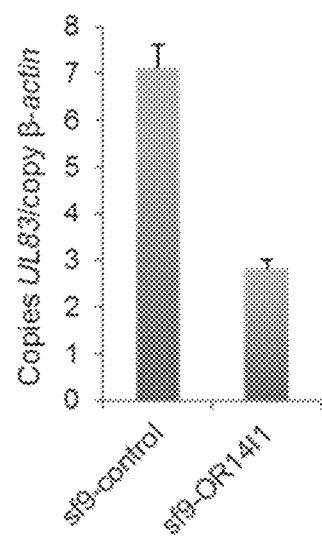

A 3D prediction model of OR14I1 and the predicted positions of four peptides exposed to the cell surface is shown in FIG. 5A. The OR14I1 structure was predicted using SWISS-MODEL with 4yay.1.A (Soluble cytochrome b562, Type-1 angiotensin II receptor) as a template and visualized using Swiss-PdbViewer 4.1.0. The amino acid sequences of four peptides represented predicted protein loops of OR14I1 on the cell surface are shown in Table 3.

TABLE 3

| name | Position (extra-cellular) | Amino acid | SEQ ID NO: |
|---|---|---|---|
| Peptide 1 | 1-26 | MDNLTKVTEFLLMEFSGIWELQVLHA | 1 |
| Peptide 2 | 77-92 | PKSIRNSLTRRSSISY | 26 |
| Peptide 3 | 163-189 | REHVCRSSVIHQFFRDIPHVLALVSCE | 27 |
| Peptide 4 | 263-269 | KALSIQD | 28 |

Figure 5C:
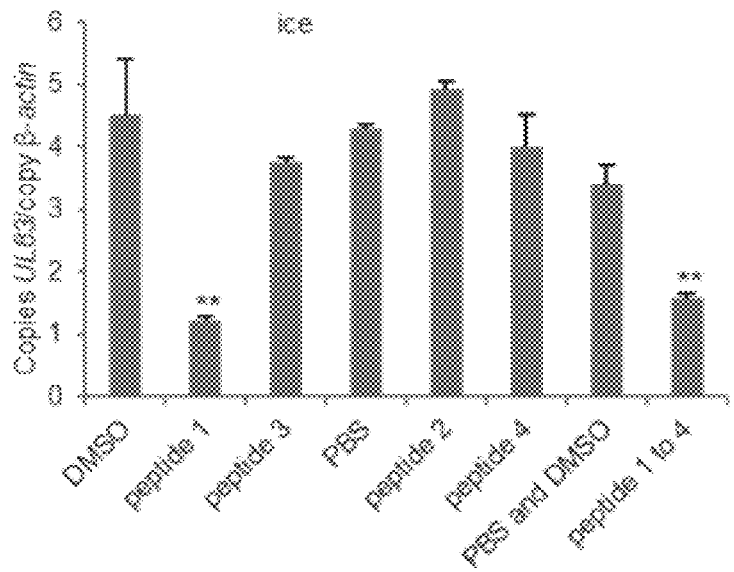
Figure 5D:
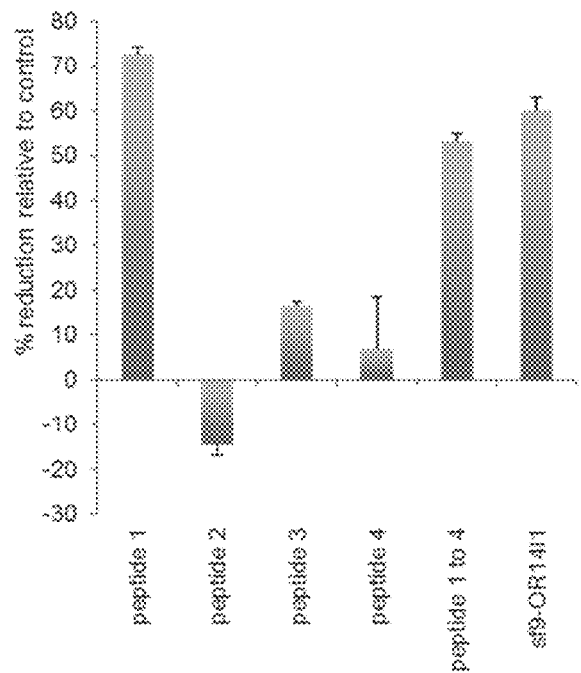

Viral binding to ARPE19 cells was evaluated in the presence of Sf9-OR14I1 membrane particles. The Sf9-OR14I1 membrane particles were pre-incubated with TB40E-GFP virus at 37° C. for 2 hours and the mixture were applied to ARPE19 cells at 4° C. for 2 h. After washing with cold PBS, viral DNA levels were quantified by qPCR. As shown in FIG. 5B, Sf9-OR14I1 was able to reduce TB40 GFP virus binding to ARPE19 epithelial cells, demonstrating that exogenous OR14I1 competes for HCMV binding to epithelial cells. In addition, four peptides shown in Table 3 (100 μg/ml each) were preincubated with TB40E-GFP virus at 37° C. for 2 h individual or in combination and the mixtures were incubated with ARPE19 cells at 4° C. for 2 h. After cold PBS washing, viral DNA levels were quantified by qPCR. The results, shown in FIGS. 5C-D, showed that N-terminal peptides of OR14I1 can prevent HCMV infection of epithelial cells.

Figure 6A:
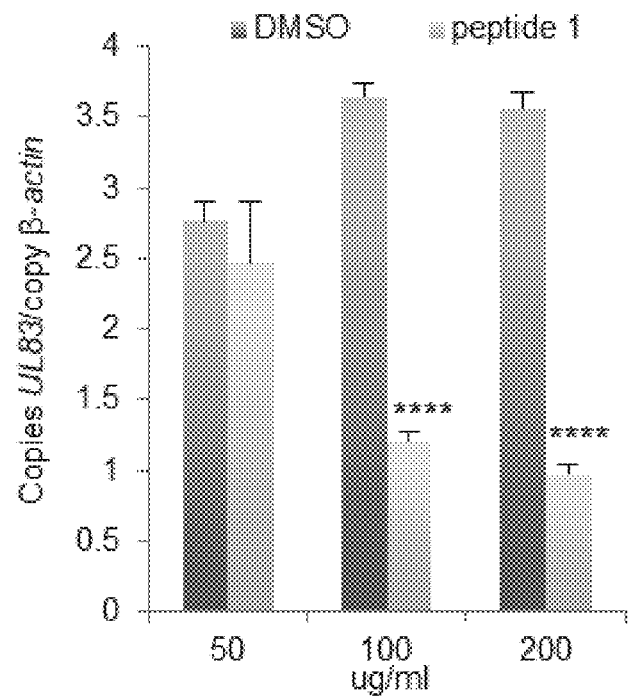
Figure 6B:
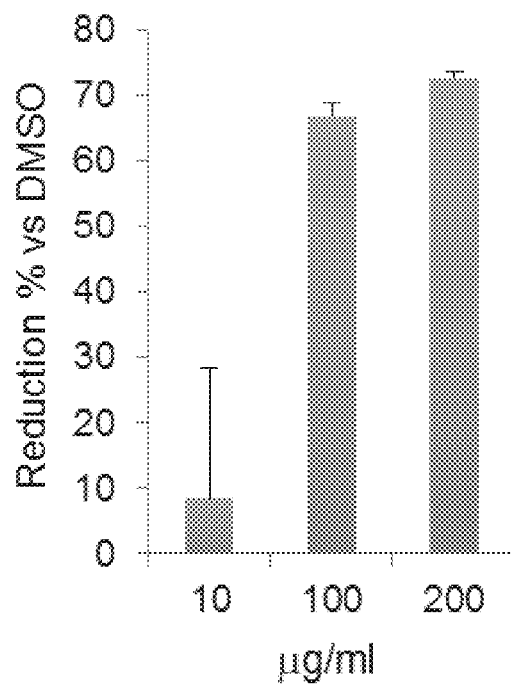
Figure 6C:
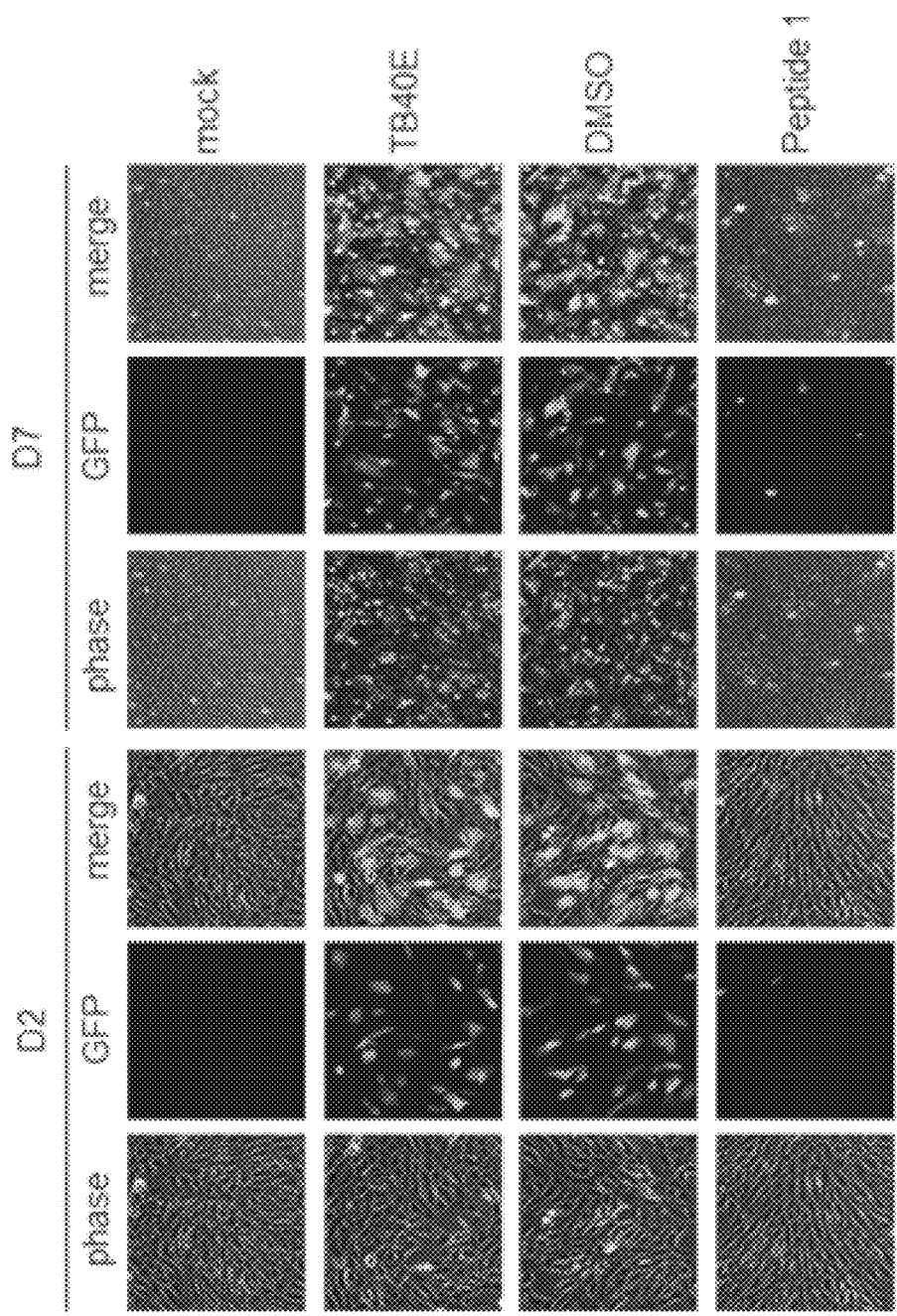
Figure 6D:
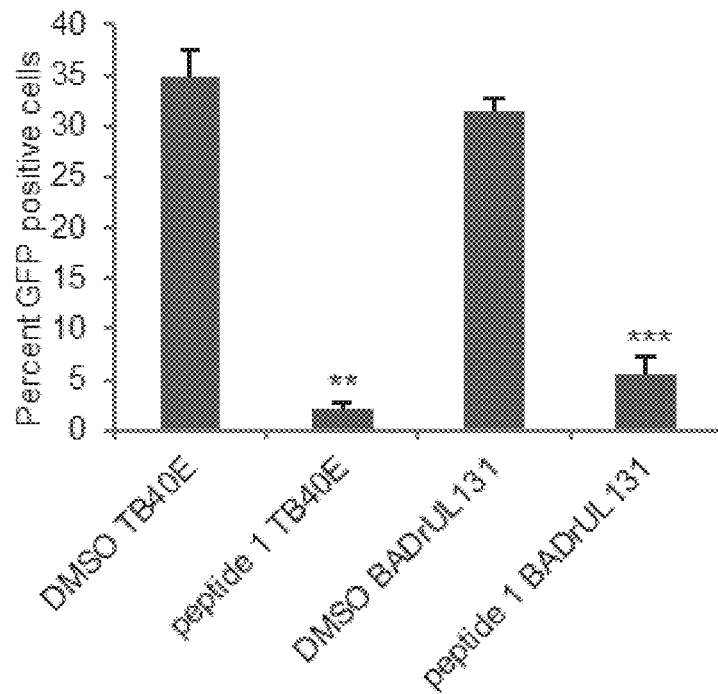
Figure 6E:
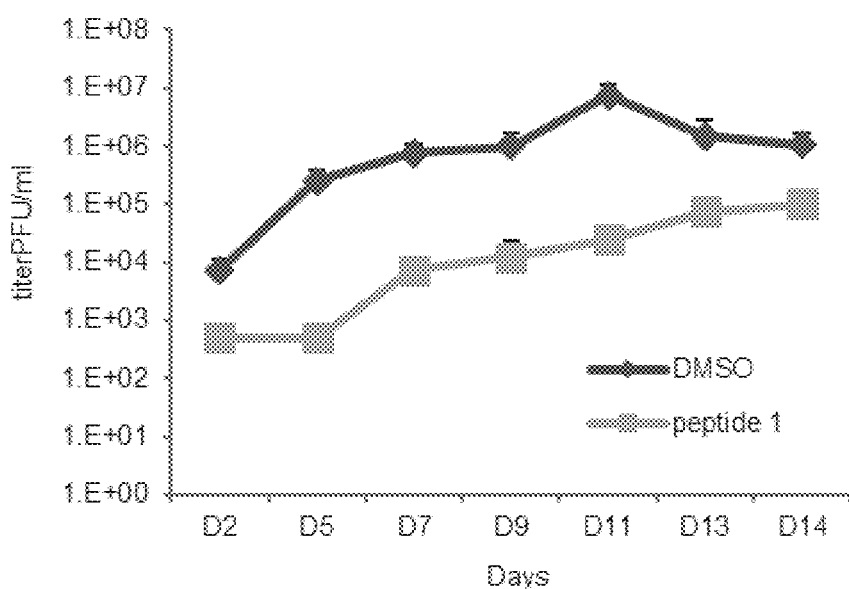

Different amounts of synthetic peptide representing the N-terminus of OR14I1 (Peptide 1) were preincubated with TB40E-GFP virus at 37° C. for 2 h and the mixture applied to ARPE19 cells at 4° C. for 2 h. After PBS washing, viral DNA levels were quantified by qPCR. As shown in FIGS. 6A-D, Peptide 1 was sufficient to prevent for TB40E-GFP virus binding ARPE19 cells. These anti-viral actions of peptide 1 were independent of viral strain (FIG. 6D), but were dependent on the presence of the PC (FIG. 9). Peptide 1 had a modest effect on PC+ HCMV infection of fibroblasts (FIG. 9) but prevented PC+ virus infection of multiple epithelial cell lines (FIG. 10). Peptide 1 also compromised the long-term replication of HCMV (FIG. 6E). Together, these results show that a peptide representing the N-terminal sequence of OR14I1 can inhibit the binding, infection, and replication of PC+ HCMV in epithelial cells.

HCMV receptor engagement and cAMP/PKA signaling was also evaluated. ARPE19 or OR14I1 knock down cells were pretreated with phosphokinase A (PKA) inhibitor H-89 (20 μM), adenylate cyclase antagonist, SQ22536 (150 μM), or adenylate cyclase activator, forskolin (FSK; 20 μM) for 2 h prior to TB40E-GFP infection (MOI=4.0). As shown in FIGS. 7A-C, H-89, SQ22536, and pep1 reduced infectivity significantly. FSK, a PKA activator, improved infection activity as expected in ARPE19 epithelial cells but not in shOR14I1 knock down ARPE19 epithelial cells, which indicated that cAMP is in the signaling pathway downstream of OR14I1.

It is evident that signaling is an important part of the early steps of virus/receptor interactions and virus entry. Without wishing to be bound by theory, it is possible that these signaling pathways are activated upon virus binding to receptors and would in turn actively induce internalization of the virus/receptor complex. Viral infections are typically associated with major impacts in the molecular physiology of host cells and altering the expression of cellular genes leading to an increased level of stress proteins and the activation of the innate immune system. In many cases, viruses also actively usurp the signaling systems of host cells to create a favorable environment for their own replication and amplification. It is clear that virus binding and internalization represent a series of events that involves numerous cellular factors, which are highly dynamics, interconnected, and coordinated in time and space. HCMV modulation of the PI(3)K/Akt pathway is an important mechanism of apoptotic inhibition, ensuring long-term virus survival, see Peppenelli et al., JVI 90: 3138-47, 2016; Cojohari et al. JVI 90: 6443-52, 2016.

To investigate HCMV-induced activation of the Akt signaling pathway, we tested whether Akt is activated upon TB40E GFP infection. As shown in FIG. 8A, TB40E stimulated the robust phosphorylation of Akt in ARPE19 cells as early as 5 min after the addition of virus. The pretreatment of ARPE19 cells with the PI3K inhibitor LY294002 clearly reduced Akt phosphorylation (and also reduced IE, E-L protein expression and virus yield; see Filippakis et al., BBA 1813: 1872-82, 2011), showing that TB40E-GFP infection triggered the activation of Akt through PI3K. To determine whether the Akt pathway is a downstream of OR14I1 signaling pathway, OR14I1 was knocked out as described above using sgRNA. In the OR14I1 knock out cells Akt phosphorylation was barely detectable, while in contrast Akt phosphorylation was clearly evident at 5 minutes after infection in control cells (FIG. 8B). These results indicated that TB40E-GFP activates the Akt pathway in an OR14I1 dependent manner.

To determine whether an agent that interferes with HCMV-OR14I1 interactions would also prevent Akt signaling, virus was preincubated with peptide 1 and the mixture was applied to the ARPE19 cells. Thirty minutes after infection, the cells were harvested and examined for Akt phosphorylation by Western blot. Akt phosphorylation induced by HCMV infection was abolished by treatment with peptide 1 which blocks virus binding to the epithelial cells such as ARPE19 (FIG. 8C). Thus, blocking viral binding to the cells using peptide 1 prevented HCMV-mediated activation of the Akt signaling pathway, an important pathway in the HCMV viral life cycle.

To narrow down the amino acids responsible for the activity of peptide 1, smaller peptides were made that included 13 amino acids, starting with each of the amino acids individually, as shown in Table 4. Each peptide was tested for the ability to inhibit HCMV infection. The results, shown in FIG. 11, indicate that peptides comprising amino acids 10-22, 11-23, and 12-24 had the best activity, while the 9-21 peptide also showed some inhibition.

TABLE 4

| Name | aa | Sequence | SEQ ID NO |
| --- | --- | --- | --- |
| 1-13aa | 1-13 | MDNLTKVTEFLLM | 29 |
| 2-14aa | 2-14 | DNLTKVTEFLLME | 30 |
| 3-15aa | 3-15 | NLTKVTEFLLMEF | 31 |
| 4-16aa | 4-16 | LTKVTEFLLMEFS | 32 |
| 5-17aa | 5-17 | TKVTEFLLMEFSG | 33 |
| 6-18aa | 6-18 | KVTEFLLMEFSGI | 34 |
| 7-19aa | 7-19 | VTEFLLMEFSGIW | 35 |
| 8-20aa | 8-20 | TEFLLMEFSGIWE | 36 |
| 9-21aa | 9-21 | EFLLMEFSGIWEL | 37 |
| 10-22aa | 10-22 | FLLMEFSGIWELQ | 38 |
| 11-23aa | 11-23 | LLMEFSGIWELQV | 39 |
| 12-24aa | 12-24 | LMEFSGIWELQVL | 40 |
| 13-25aa | 13-25 | MEFSGIWELQVLH | 41 |
| 14-26aa | 14-26 | EFSGIWELQVLHA | 42 |

REFERENCES

1. Shalem O, Sanjana N E, Hartenian E, Shi X, Scott D A, Mikkelsen T S, Heckl D, Ebert B L, Root D E, Doench J G, Zhang F. 2014. Genome-scale CRISPR-Cas9 knockout screening in human cells. Science 343: 84-87.
2. E X, Pickering M T, Debatis M, Castillo J, Lagadinos A, Wang S, Lu S, Kowalik T F. 2011. An E2F1-mediated DNA damage response contributes to the replication of human cytomegalovirus. PLoS Pathog 7:e1001342.
3. Gault E, Michel Y, Dehee A, Belabani C, Nicolas J C, Garbarg-Chenon A. 2001. Quantification of human cytomegalovirus DNA by real-time PCR. J Clin Microbiol 39:772-775.
4. Hanfler J, Kreuzer K A, Laurisch K, Rayes N, Neuhaus P, Schmidt C A, Oettle H. 2003. Quantitation of cytomegalovirus (hCMV) DNA and beta-actin DNA by duplex real-time fluorescence PCR in solid organ (liver) transplant recipients. Med Microbiol Immunol 192:197-204.
5. Wang D, Shenk T. 2005. Human cytomegalovirus virion protein complex required for epithelial and endothelial cell tropism. Proc Natl Acad Sci USA 102:18153-18158.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising an inhibitor of Olfactory Receptor Family 14 Subfamily 1 Member 1 (OR14I1), wherein the inhibitor of OR14I1 is a N-terminal peptide of OR14I1 comprising the amino acid sequence MDNLTKVTEFLLMEFSGIWELQVLHA (SEQ ID NO:1), or an active fragment thereof, and a pharmaceutically acceptable carrier.

2. The composition of claim 1, wherein the active fragment comprises FLLMEFSGIWELQ (SEQ ID NO:3), LLMEFSGIWELQV (SEQ ID NO:4), LMEFSGIWELQVL (SEQ ID NO:5), or LMEFSGIWELQ (SEQ ID NO:6).

3. The composition of claim 1, further comprising an inhibitor of adenylyl cyclases selected from the group consisting of 9-Cyclopentyladenine monomethanesulfonate; 2',5'-Dideoxyadenosine; 2',5'-Dideoxyadenosine 3'-triphosphate tetrasodium salt; Dihomo-gamma-linolenylethanolamide; KH7; LRE1; MDL-12330A; NKY80; SB-268262; BPIPP; SKF 83566; and SQ 22,536.

4. The composition of claim 1, wherein the peptide is modified.

5. The composition of claim 4, wherein the modified peptide comprises one or more D amino acids, artificial amino acids analogs, or a lipophilic substituent linked to an amino acid.

* * * * *

UNITED STATES PATENT AND TRADEMARK OFFICE
CERTIFICATE OF CORRECTION

| | | |
|---|---|---|
| PATENT NO. | : 12,268,901 B2 | Page 1 of 1 |
| APPLICATION NO. | : 17/933709 | |
| DATED | : April 8, 2025 | |
| INVENTOR(S) | : Timothy F. Kowalik, Xiaofei E and Abraham L. Brass | |

It is certified that error appears in the above-identified patent and that said Letters Patent is hereby corrected as shown below:

In the Claims

In Column 57, Line 51 (approx.), Claim 1, delete "Subfamily 1" and insert -- Subfamily I --

Signed and Sealed this
Twenty-second Day of July, 2025

Coke Morgan Stewart
*Acting Director of the United States Patent and Trademark Office*